United States Patent [19]

Janoff et al.

[11] Patent Number: 4,891,208

[45] Date of Patent: * Jan. 2, 1990

[54] STEROIDAL LIPOSOMES

[75] Inventors: Andrew S. Janoff, Yardley, Pa.; Mircea C. Popescu; Alan L. Weiner, both of Plainsboro; Lois E. Bolscak, Lawrenceville; Paul A. Tremblay, Hamilton; Christine E. Swenson, Plainsboro, all of N.J.

[73] Assignee: The Liposome Company, Inc., Princeton, N.J.

[*] Notice: The portion of the term of this patent subsequent to Jan. 26, 2005 has been disclaimed.

[21] Appl. No.: 773,429

[22] Filed: Sep. 10, 1985

Related U.S. Application Data

[63] Continuation-in-part of Ser. No. 721,630, Apr. 10, 1985, Pat. No. 4,721,612, which is a continuation-in-part of Ser. No. 599,691, Apr. 12, 1984, abandoned.

[51] Int. Cl.$^4$ ............................................. A61K 43/00
[52] U.S. Cl. ..................................... 424/1.1; 264/4.1; 264/4.6; 424/7.1; 424/450; 428/402.2; 436/829; 514/3; 514/78; 514/167; 514/396; 514/885; 514/887; 514/967; 604/891.1
[58] Field of Search ................................ 264/4.1, 4.6; 428/402.2; 424/1.1, 7.1, 450; 514/78, 167, 887, 967; 436/829; 604/891

[56] References Cited

U.S. PATENT DOCUMENTS

| | | | |
|---|---|---|---|
| 3,932,657 | 1/1976 | Rahmann | 514/574 |
| 3,957,971 | 5/1976 | Oleniacz | 252/DIG. 13 |
| 4,177,350 | 12/1979 | Zirngibl et al. | 514/967 X |
| 4,183,847 | 1/1980 | Deshmukh | 436/13 X |
| 4,235,871 | 11/1980 | Papahadjopoulos et al. | 264/4.6 X |
| 4,271,196 | 6/1981 | Schmidt | 514/786 |
| 4,298,594 | 11/1981 | Sears et al. | 424/38 X |
| 4,342,739 | 8/1982 | Kakimi et al. | 428/402.2 X |
| 4,356,167 | 10/1982 | Kelly | 424/450 |
| 4,411,894 | 10/1983 | Schrank et al. | 514/314 X |
| 4,438,052 | 3/1984 | Weder et al. | 264/4.6 |
| 4,508,703 | 4/1985 | Redziniak et al. | 428/402.2 X |
| 4,621,053 | 11/1986 | Sugimoto | 435/68 |
| 4,721,612 | 1/1988 | Janoff et al. | 424/1.1 |

FOREIGN PATENT DOCUMENTS

WO85/04578 10/1985 PCT Int'l Appl. ................ 424/1.1
2021262 11/1979 United Kingdom.

OTHER PUBLICATIONS

Brockerhoff, H. et al. (1982), Preparation and Structural Studies of Cholesterol Bilayers, Chemical Abstracts, 97:254, No. 198451z; Biochim. Biophys. Acta. (1982), 691:227-232.
Lai, M-Z et al. (1985), Effects of Replacements of the Hydroxyl Group of Cholesterol and Tocopherol on the Thermotropic Behavior of Phospholipid Membranes, Biochemistry, 24:1646-53.
Hackh's Chemical Dictionary, Fourth Edition, revised and edited by J. Grant, McGraw-Hill Book Co., 1969, p. 698.
Gregoriadis: "The Carrier Potential of Liposomes in Biology and Medicine," The New England Journal of Medicine, vol. 295, No. 13, Sep. 23, 1976, pp. 704-710.
Shinitzky et al.: "Effective Tumor Immunization Induced by Cells of Elevated Membrane-Lipid Microviscosity," Proc. Natl. Acad. Sci., U.S.A., vol. 76, No. 10, pp. 5313-5316, Oct. 1979.
Martindale: The Extra Pharmacopoeia, 28th Edition, edited by J. Reynolds, The Pharmaceutical Press, London, 1982, p. 1759.
Ellens et al.: "pH-Induced Destabilization of Phosphatidylethanolamine-Containing Liposomes," Biochemistry, 1984, 23, 1532-1538, Mar. 27, 1984.
Chemical Abstracts, vol. 97, 1982, p. 264, 194848d & 194851z.

Primary Examiner—Richard D. Lovering
Attorney, Agent, or Firm—Allen Bloom; Thomas M. Saunders

[57] ABSTRACT

Steroidal liposomes comprising a bioactive agent and method for their administration are disclosed, the bilayers of said steroidal liposomes comprising a salt form of a carboxylic acid derivative of a sterol, a salt form of a polycarboxylic acid derivative of a sterol, a salt form of a hydroxy carboxylic acid derivative of a sterol, a salt form of an amino acid derivative of a sterol or a salt form of a poly (amino acid) derivative of a sterol; or a salt form of an organic acid derivative of cholesterol, a vitamin D, a phytosterol, or a steroidal hormone.

46 Claims, 9 Drawing Sheets

STEROIDAL LIPOSOMES

This is a continuation-in-part of a co-pending application Ser. No. 721,630, filed Apr. 10, 1985, and now U.S. Pat. No. 4,721,612, which is a continuation-in-part of patent application Ser. No. 599,691, filed Apr. 12, 1984, now abandoned.

| | | TABLE OF CONTENTS | |
|---|---|---|---|
| | | | Page |
| 1. | Field of the Invention | | 4 |
| 2. | Background of the Invention | | 4 |
| | 2.1 | Liposomes | 4 |
| | 2.2 | Water-Soluble Sterols | 7 |
| 3. | Summary of the Invention | | 9 |
| 4. | Brief Description of the Figures | | 11b |
| 5. | Detailed Description of the Invention | | 12 |
| 6. | Example: Cholesterol Hemisuccinate Liposomes Entrapping Water-Soluble Compounds | | 28 |
| | 6.1 | Liposomes prepared Using Various Salt Forms of Cholesterol Hemisuccinate | 29 |
| | | 6.1.1 Tris-Salt Cholesterol Hemisuccinate MLVs | 29 |
| | | 6.1.2 2-Amino-2-Methyl-1, 3-Propanediol Cholesterol Hemisuccinate-MLVs | 29 |
| | | 6.1.3 2-Aminoethanol Cholesterol Hemisuccinate-MLVs | 30 |
| | | 6.1.4 Bis-Tris-Propane Cholesterol Hemisuccinate-MLVs | 30 |
| | | 6.1.5 Triethanolamine Cholesterol Hemisuccinate-MLVs | 31 |
| | | 6.1.6 Miconazole Cholesterol Hemisuccinate-MLVs | 31 |
| | | 6.1.7 Cholesterol Hemisuccinate-SUVs Prepared by Sonication | 31 |
| | | 6.1.8 Cholesterol Hemisuccinate-SUVs Prepared by Extrusion Techniques | 32 |
| | | 6.1.9 Miconazole - CHS-Tris Cream | 33 |
| | | 6.1.10 Terconazole - CHS-Tris Cream | 34 |
| | | 6.1.11 Miconazole - CHS-Tris Suppository | 34 |
| | | 6.1.12 In Vivo Activity for Vaginal Candida Infections | 35 |
| | 6.2 | Entrapment of Inulin in Cholesterol Hemisuccinate MLVs | 36 |
| | | 6.2.1 Encapsulation Efficiency of Inulin in Cholesterol Hemisuccinate-MLVs and Egg Phosphatidylcholine-MLVs | 37 |
| | 6.3 | Entrapment of Inulin in Cholesterol Hemisuccinate-SUVs | 40 |
| | 6.4 | Entrapment of Chromium in Cholesterol Hemisuccinate-MLVs | 41 |
| | | 6.4.1 Encapsulation Efficiency of Chromium in Cholesterol Hemisuccinate-MLVs | 41 |
| | | 6.4.2 Captured Volume in Cholesterol Hemisuccinate-MLVs: Chromium Entrapment and Cholesterol Hemisuccinate Concentration | 42 |
| | 6.5 | Ultrastructure of Cholesterol Hemisuccinate Liposomes | 43 |
| | 6.6 | X-Ray Diffraction Analysis of Cholesterol Hemisuccinate Liposomes | 44 |
| | 6.7 | Electron Spin Resonance Analysis of Cholesterol Hemisuccinate Liposomes | 46 |
| | 6.8 | Isotonic Swelling of Cholesterol Hemisuccinate Liposomes | 47 |
| 7. | Example: Cholesterol Hemisuccinate Liposomes Entrapping Sparingly Soluble Compounds | | 48 |
| | 7.1 | Bovine Growth Hormone Entrapped in Cholesterol Hemisuccinate-SUVs | 48 |
| | 7.2 | Insulin Entrapped in Cholesterol Hemisuccinate SUVs | 49 |
| | 7.3 | Tylosin Entrapped in Cholesterol Hemisuccinate-SUVs | 50 |
| 8. | Example: The Use of Cholesterol Hemisuccinate Liposomes to Entrap Lipid Soluble Compounds | | 51 |
| | 8.1 | Indomethacin Entrapped in Cholesterol Hemisuccinate-MLVs | 51 |
| | | 8.1.2 Ultrastructure of Cholesterol Hemisuccinate Vesicles Containing Indomethacin | 52 |
| | 8.2 | Diazepam Entrapped in Cholesterol Hemisuccinate-SUVs | 53 |
| 9. | Example: The Use of Cholesterol Hemisuccinate Liposomes to Determine Aminoglycoside Concentration in Serum | | 55 |

-continued

TABLE OF CONTENTS

| | | | Page |
|---|---|---|---|
| 10. | Example: In Vivo Administration of Cholesterol Hemisuccinate Liposomes | | 56 |
| | 10.1 | Treatment of Joint Arthritis Using Indomethacin Entrapped in Cholesterol Hemisuccinate-MLVs | 56 |
| | 10.2 | In Vivo Administration of Diazepam Entrapped in Cholesterol Hemisuccinate SUVs | 57 |
| | | 10.2.1 Organ Distribution After Intravenous Innoculation | 58 |
| | 10.3 | In Vivo Administration of Chromium Entrapped in Cholesterol Hemisuccinate-MUVs | 59 |
| | 10.4 | In Vivo Administration of Human Growth Hormone Entrapped in Cholesterol Hemisuccinate MLVs | 61 |

FIELD OF THE INVENTION

The present invention relates to methods and compositions for the entrapment of compounds in liposomes composed of salt forms of organic acid derivatives of sterols that are capable of forming bilayers.

Sterols such as cholesterol or other lipids, to which a hydrophilic moiety such as a salt form of an organic acid is attached, can be used to prepare suspensions of multilamellar or small unilamellar vesicles. The sterol liposomes of the present invention may be prepared with or without the use of organic solvents. These vesicles may entrap water-soluble compounds, partially water-soluble compounds, and water-insoluble compounds.

The sterol vesicles described herein are particularly useful for the entrapment of biologically active compounds or pharmaceutical compounds which can be administered in vivo. Alternatively, the sterol liposomes of the present invention may be used in vitro. For instance, the cholesterol hemisuccinate liposomes described herein may be used in vitro in divalent cation-dependent assay systems.

BACKGROUND OF THE INVENTION

2.1. LIPOSOMES

Liposomes are completely closed bilayer membranes containing an encapsulated aqueous phase. Liposomes may be any variety of multilamellar vesicles (onion-like structures characterized by concentric membrane bilayers each separated by an aqueous layer) or unilamellar vesicles (possessing a single membrane bilayer).

Two parameters of liposome preparations are functions of vesicle size and lipid concentration: (1) Captured volume, defined as the volume enclosed by a given amount of lipid, is expressed as units of liters entrapped per mole of total lipid (1 $mol^{-1}$). The captured volume depends upon the radius of the liposomes which in turn is affected by the lipid composition of the vesicles and the ionic composition of the medium. (2) Encapsulation efficiency, defined as the fraction of the aqueous compartment sequestered by the bilayers, is expressed as a percentage. The encapsulation efficiency is directly proportional to the lipid concentration; when more lipid is present, more solute can be sequestered within liposomes. (See Deamer and Uster, 1983, Liposome Preparation: Methods and Mechanisms, in *Liposomes*, ed. M. Ostro, Marcel Dekker, Inc., NY, pp. 27–51.)

The original method for liposome preparation (Bangham et al., 1965, J. Mol. Biol. 13: 238–252) involved suspending phospholipids in an organic solvent which was then evaporated to dryness leaving a waxy deposit of phospholipid on the reaction vessel. Then an appropriate amount of aqueous phase was added, the mixture was allowed to "swell," and the resulting liposomes which consisted of multilamellar vesicles (hereinafter referred to as MLVs) were dispersed by mechanical means. The structure of the resulting membrane bilayer is such that the hydrophobic (non-polar) "tails" of the lipid orient toward the center of the bilayer while the hydrophilic (polar) "heads" orient towards the aqueous phase. This technique provided the basis for the development of the small sonicated unilamellar vesicles (hereinafter referred to as SUVs) described by Papahadjopoulos and Miller (1967, Biochim. Biophys. Acta. 135: 624–638). Both MLVs and SUVs, however, have limitations as model systems.

In attempts to increase captured volume or encapsulation efficiency a number of methods for the preparation of liposomes comprising physpholipid bilayers have been developed; however, all methods require the use of organic solvents. Some of these methods are briefly described below.

An effort to increase the encapsulation efficiency involved first forming liposome precursors or micelles, i.e., vesicles containing an aqueous phase surrounded by a monolayer of lipid molecules oriented so that the polar head groups are directed towards the aqueous phase. Liposome precursors are formed by adding the aqueous solution to be encapsulated to a solution of polar lipid in an organic solvent and sonicating. The liposome precursors are then emulsified in a second aqueous phase in the presence of excess lipid and evaporated. The resultant liposomes, consisting of an aqueous phase encapsulated by a lipid bilayer are dispersed in aqueous phase (see U.S. Pat. No. 4,224,179 issued Sept. 23, 1980 to M. Schneider).

In another attempt to maximize the encapsulation efficiency, Papahadjopoulos (U.S. Pat. No. 4,235,871 issued Nov. 25, 1980) describes a "reverse-phase evaporation process" for making oligolamellar lipid vesicles also known as reverse-phase evaporation vesicles (hereinafter referred to as REVs). According to this procedure, the aqueous material to be encapsulated is added to a mixture of polar lipid in an organic solvent. Then a homogeneous water-in-oil type of emulsion is formed and the organic solvent is evaporated until a gel is formed. The gel is then converted to a suspension by dispersing the gel-like mixture in an aqueous media. The REVs produced consist mostly of unilamellar vesicles (large unilamellar vesicles, or LUVs) and some oligolamellar vesicles which are characterized by only a few concentric bilayers with a large internal aqueous space.

Much has been written regarding the possibilities of using liposomes for drug delivery systems. See, for example, the disclosures in U.S. Pat. No. 3,993,754 issued on Nov. 23, 1976, to Yeuh-Erh Rahman and Elizabeth A. Cerny, and U.S. Pat. No. 4,145,410 issued on Mar. 20, 1979, to Barry D. Sears. In a liposome drug delivery system the medicament is entrapped during liposome formation and then administered to the patient to be treated. The medicament may be soluble in water or in a non-polar solvent. Typical of such disclosures are U.S. Pat. No. 4,235,871 issued Nov. 25, 1980, to Papahadjopoulos and Szoka and U.S. Pat. No. 4,224,179, issued Sept. 23, 1980 to M. Schneider. When preparing liposomes for use in vivo it would be advantageous (1) to eliminate the necessity of using organic solvents during the preparation of liposomes; and (2) to maximize the encapsulation efficiency and captured volume so that a greater volume and concentration of the entrapped material can be delivered per dose.

2.2. Water-Soluble Sterols

A variety of sterols and their water soluble derivatives have been used for cosmetic, pharmaceutical and diagnostic purposes. Of the water soluble sterols, for example, branched fatty acid cholesterol esters, steroid esters and PEG-phytosterols have been used in cosmetic preparations (European patent application No. 28,456; U.S. Pat. No. 4,393,044; and Schrader, Drug and Cosmetic Industry, Sept. 1983, p.33 and Oct. 1983, p.46). Thakkar and Kuehn (1969, J. Pharm. Sci. 58(7): 850–852) disclose the solubilization of steroid hormones using aqueous solutions of steroidal non-ionic surfactants, specifically ethoxylated cholesterol (i.e., PEG-cholesterol) at a concentration of 1–5%. However, the effectiveness or utility of the solubilized steroid hormones in vivo was not demonstrated. A number of water soluble cholesterols have been prepared and used as water-soluble standards for the determination of cholesterol levels in biological fluids (U.S. Pat. Nos. 3,859,047; 4,040,784; 4,042,330; 4,183,847; 4,189,400; and 4,224,229). Shinitzky et al. (1979, Proc. Natl. Acad. Sci. USA 76:5313–5316) incubated tumor cells in tissue culture medium containing a low concentration of cholesterol and cholesteryl hemisuccinate. Incorporation of cholesterol or cholesteryl hemisuccinate into the cell membrane decreased membrane fluidity and increased membrane-lipid microviscosity.

Cholesterol and other sterols, have also been incorporated into phospholipid liposome membranes in order to alter the physical properties of the lipid bilayers. For example, in a recent abstract, Ellens et al. (1984, Biophys. J. 45: 70a) discuss the effect of H+ on the stability of lipid vesicles composed of phosphatidylethanolamine and cholesteryl hemisuccinate. In fact, Brockerhoff and Ramsammy (1982, biochim. Biophys. Acta. 691:227–232) reported that bilayers can be constructed which consist entirely of cholesterol, provided a stabilizing hydrophilic anchor is supplied. Multilamellar and unilamellar cholesterol liposomes were prepared in a conventional manner described above evaporating to dryness the cholesterol derivatives (i.e., cholesterol-phosphocholine, cholesterolpolyethylene glycol, or cholesterol-SO4) dispersed in an organic solvent leaving a lipid film deposited in the reaction vessel. The lipid films were sonicated under 2 ml water using an ultrasonic homogenizer with a microtip. Formation of multilamellar vesicles required 10 minutes sonication, whereas formation of small unilamellar vesicles required 4 hours of sonication. The resulting suspensions of multilamellar liposomes were milky whereas the suspensions of unilamellar liposomes were transparent.

However, the ability to efficiently entrap bioactive agents in sterol vesicles which are suitable for administration in vivo to provide for the administration of higher doses of water-soluble agents and to facilitate the administration of water-insoluble agents has not heretofore been explored.

SUMMARY OF THE INVENTION

The present invention involves methods and compositions for the entrapment of various compounds in liposomes, the bilayers of which comprise salt forms of organic acid derivatives of sterols. Entrapment of a compound is defined herein as the encapsulation of a water-soluble compound in the aqueous compartment of the liposome or the entrapment of a water-insoluble compound within the sterol bilayer. The tris(hydroxymethyl)aminomethane salt (tris-salt) form of organic acid derivatives of sterols are particularly useful as the vesicle bilayer ingredient.

The method for preparing the sterol vesicles involves adding to an aqueous buffer a salt form of an organic acid derivative of a sterol capable of forming closed bilayers in an amount sufficient to form completely closed bilayers which entrap an aqueous compartment. A suspension of multilamellar vesicles is formed by shaking the mixture. The formation of vesicles is facilitated if the aqueous buffer also contains the counterion of the salt in solution. Furthermore, if the dissociated salt form of the organic acid derivative of a sterol is negatively charged at neutral pH, the aqueous buffer should be essentially free of divalent or multivalent cations. Similarly, when the dissociated salt form of the organic acid derivative of a sterol is positively charged at neutral pH, the aqueous buffer should be essentially free of multivalent anions. The application of energy to the suspension, e.g., sonication, or extrusion of the vesicles through a French pressure cell (French Press) or through a porous filter of the appropriate pore size, will convert the multilamellar sterol vesicles to unilamellar vesicles.

In order to entrap a water-soluble compound, a partially water-soluble compound or a water-insoluble compound in the sterol vesicles of the present invention, a number of approaches are possible. Compounds which either partition into the sterol bilayers (e.g., water-insoluble compounds) or water-soluble compounds may be added to the aqueous phase before formation of the vesicles in order to entrap the agent within the vesicles during formation. Alternatively, compounds which are water-insoluble or lipid soluble may be added to the suspension of sterol vesicles after the vesicles are formed, in which case the compound partitions into the sterol bilayers. In another embodiment, a water-soluble compound and the salt-form of an organic acid derivative of a sterol may be added to an organic solvent so that both are solubilized (co-solubilized). The organic solvent may then be evaporated leaving a film containing a homogeneous distribution of the water-insoluble compound and the sterol derivative. Sterol liposomes entrapping the water-insoluble compounds are formed when an aqueous buffer is added to the film with shaking.

The sterol liposomes of the present invention are particularly advantageous when used to entrap water-insoluble bioactive agents or those that are sparingly soluble in water. This enables the administration in vivo of water-insoluble drugs; and furthermore, it allows for the administration in vivo of high concentrations of the water insoluble compounds, because it allows alteration of the dose:volume ratio. The sterol vesicles of the present invention offer similar advantages when used to entrap water soluble bioactive agents. In addition, the sterol vesicles of the present invention may be used in diagnostic assays in vitro.

The present invention affords a number of advantages in that the sterol vesicles:

(1) are formed easily and rapidly;

(2) have high encapsulation efficiencies as compared with phospholipid MLVs;

(3) do not require the use of organic solvents for their preparation (although the sterol vesicles of the present invention can be prepared using organic solvents); and (4) can entrap a bioactive or pharmaceutical agent, which when administered in vivo, is released and metabolized. The fate of the entrapped agent in vivo depends upon the mode of administration.

The present invention is further directed to a composition comprising the tris(hydroxymethyl)aminomethane salt of cholesteryl hemisuccinate and an antifungal compound, particularly when the antifungal agent is miconazole, terconazole or econazole, isoconazole, tioconazole, bifonazole, clotrimazole, ketoconazole, butaconazole, itraconazole, oxiconazole, fenticonazole, nystain, naftifine, amphotericin B, zinoconazole or ciclopirox olamine. The composition can be used to treat a fungal infection and can be administered topically including orally or intravaginally.

The present invention includes a composition comprising the tris(hydroxymethyl)aminomethane salt of cholesteryl hemisuccinate and a peptide, particularly a hydrophobic peptide, human growth hormone, bovine growth hormone, porcine growth hormone or insulin. The composition can be administered to increase milk production or to increase or initiate growth of a mammal.

DETAILED DESCRIPTION OF THE INVENTION

Figure 1:
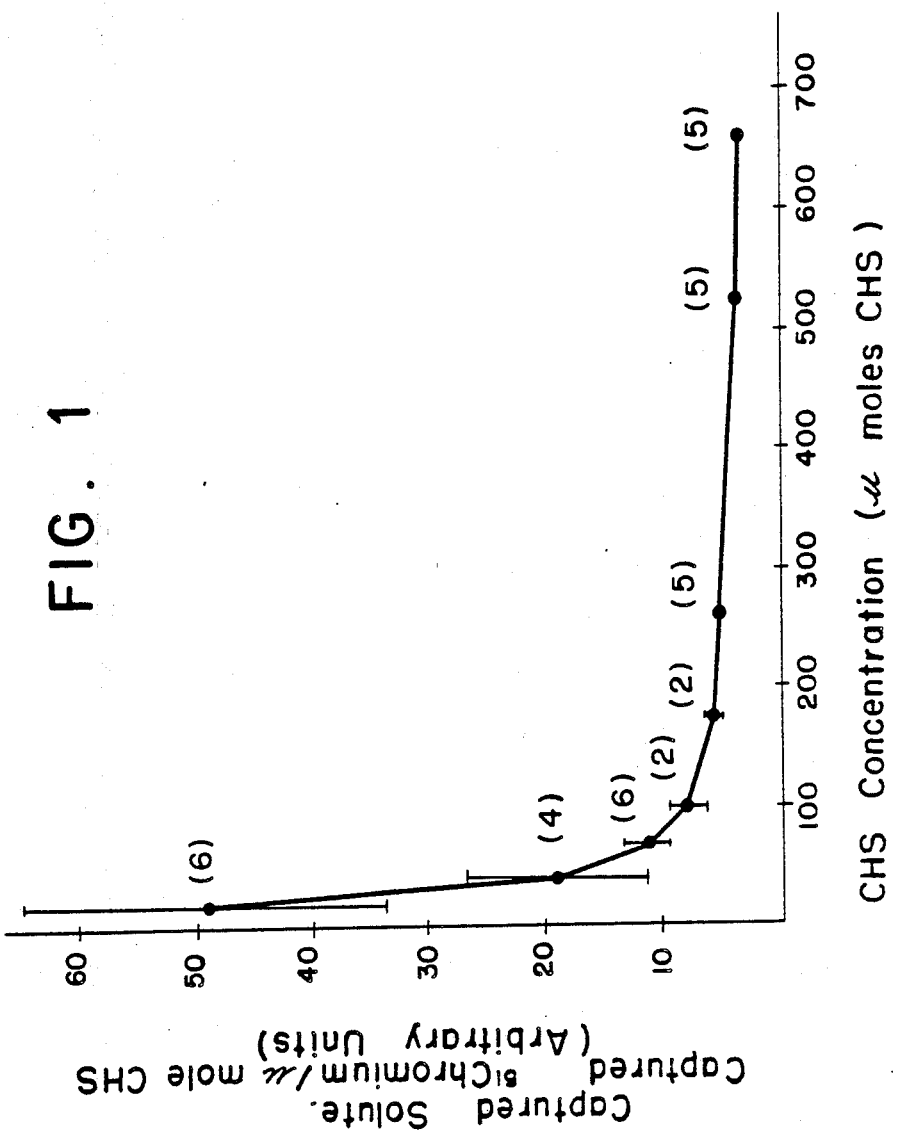
FIG. 1 graphically demonstrates the inverse relationship of the captured solute (chromium) and the concentration of cholesterol hemisuccinate used to prepare the multilamellar liposomes.

The present invention describes methods and compositions for the entrapment of water-soluble, partially water-soluble, or water-insoluble compounds in liposomes, the bilayers or which comprise salt forms of organic acid derivatives of sterols that are capable of forming closed bilayers. Accordingly, the sterol liposomes of the present invention can be prepared to (1) entrap a water-soluble compound in the aqueous compartment; or (2) entrap a water-insoluble compound which partitions into the sterol bilayers; or (3) both entrap a water-soluble compound and entrap a water-insoluble compound in one liposome preparation.

Any salt form of an organic acid derivative of a sterol which is capable of forming completely closed bilayers in aqueous solutions (i.e., liposomes) may be used in the practice of the invention. The suitability of a particular salt-form of an organic acid derivative of a sterol depends upon its ability to sequester a water-soluble compound so that the compound is not in contact with the outside environment.

To determine definitively that entrapment within the aqueous compartment of any liposome has occurred, the following criteria have been established (See Sessa and Weissmann, 1970, J. Biol. Chem. 245:3295): (a) there must be a clear separation of free from sequestered compound as assayed by gel filtration; (b) there must be no hydrophobic or charge-charge interaction between the outermost vesicle bilayer and the entrapped compound since this may result in a failure to achieve separation of the free compound from the liposomes by molecular sieving, thereby artificially increasing the apparent sequestration or encapsulation efficiency. To eliminate this possibility it must be shown that the water-soluble compound added to a suspension of previously formed liposomes does not coelute with preformed liposomes; (c) disruption of gel-filtered liposomes by use of detergents or other membrane perturbants must induce a shift in the gel filtration pattern of the sequestered molecule from a position coincident with the liposome peak to one that coelutes with the free molecule.

Generally any sterol which can be modified by the attachment of an organic acid may be used in the practice of the present invention. For example, such sterols include but are not limited to cholesterol, vitamin D, phytosterols (including but not limited to sitosterol, campesterol, stigmasterol, and the like), steroid hormones, and the like.

Organic acids which can be used to derivatize the sterols include but are not limited to the carboxylic acids, dicarboxylic acids, polycarboxylic acids, hydroxy acids, amino acids and polyamino acids. Because the salt forms increase the water solubility of organic acids, any organic acid may be used to derivatize the sterols; however an advantage may be obtained if the organic acid moiety itself is water soluble. Such water-soluble organic acid moieties include but are not limited to water-soluble aliphatic carboxylic acids such as acetic, propionic, butyric, valeric acids and the like (N.B., up to four-carbon acids are miscible with water; the five-carbon free acid is partly soluble and the longer chain free acids are virtually insoluble); water-soluble aliphatic dicarboxylic acids such as malonic, succinic, glutaric, adipic, pimelic, maleic and the like (N.B., the shorter chains are appreciably more soluble in water;

borderline solubility in water occurs at $C_6$ to $C_7$); and water-insoluble aromatic dicarboxylic acids such as hemimellitic, trimesic, succinimide, and the like; polycarboxylic acids; water-soluble hydroxy acids such as glycolic, lactic, mandelic, glyceric, malic, tartaric, citric, and the like (N.B., α-hydroxy acids containing a branched chain attached to the α-carbon of the carbonyl group would be less susceptible to hydrolysis and, therefore, advantageous in the practice of the present invention); and any of the amino acids and polyamino acids.

The organic acid can be linked to an hydroxyl group of the sterol via an ester or an ether bond using conventional methods (see, for example, U.S. Pat. Nos. 3,859,047; 4,040,784; 4,042,330; 4,183,847; and 4,189,400). The salt forms of the derivatized sterols can be prepared by dissolving both the organic acid derivative of the sterol and the counterion of the salt (e.g., the free base of the salt) in an appropriate volatile solvent, and removing the solvent by evaporation or a similar techique leaving a residue which consists of the salt form of the organic acid derivative of the sterol. Counterions that may be used include, but are not limited to, tris, 2-amino-2-methyl-1,3-propanediol, 2-aminoethanol, bis-tris propane, triethanolamine, and the like to form the corresponding salt. In fact, the free base of an ionizable bioactive agent such as miconazole free base and the like may be used as the counterion. Thus, the bioactive agent can be used as a counterion.

The sterol liposomes of the present invention may be prepared by adding to an aqueous phase a salt form of an organic acid derivative of a sterol capable of forming bilayers so that the derivatized sterol is present in an amount sufficient to form vesicles (i.e., completely closed bilayers containing an entrapped aqueous compartment). The preparation is then shaken until a milky suspension of multilamellar sterol vesicles is formed. In the preferred embodiment, the aqueous phase should contain the salt in solution to facilitate vesicle formation. Furthermore, if the dissociated salt form of the organic acid derivative of the sterol is negatively charged at neutral pH, the aqueous buffer should be essentially free of multivalent cations. Similarly, when the dissociated salt form of the organic acid derivative is positively charged at neutral pH, the aqueous buffer should be essentially free of multivalent anions.

In complete contrast to reported methods for multilamellar vesicle formation (e.g., phospholipid vesicles or the cholesterol liposomes of Brockerhoff and Ramsammy, 1982, Biochim. Biophys. Acta. 691: 227–232), the method for the formation of the sterol multilamellar vesicles of the present invention does not require the use of organic solvents. Furthermore, unlike the method of Brockerhoff and Ramsammy (supra) sonication is not necessary to form the sterol multilamellar vesicles. In fact, sonication of the milky suspension of sterol multilamellar vesicles of the present invention, or the use of a French press (SLM-Aminco, Urbana, ILL) followed by sonication may be used to convert the milky suspension of multilamellar sterol vesicles to a clear suspension of unilamellar sterol vesicles. Similarly, multiple extrusions of the multilamellar sterol vesicles at moderate pressures through a filter having a pore size of equal to or less than 100 nm in diameter can be employed to obtain unilamellar sterol vesicles. This extrusion technique is described in detail in co-pending application Ser. No. 622,690 filed Jun. 20, 1984 and now abandonded by Cullis et al. for "Extrusion Technique for Producing Unilamellar Vesicles" which is incorporated by reference herein.

As previously explained, the tris-salt form of any organic acid derivative of a sterol may be advantageously used in the practice of the present invention. For example, the tris-salt form of a sterol hemi-dicarboxylic acid such as a sterol hemisuccinate or a mixture of sterol hemisuccinates are particularly useful for forming the vesicle bilayers of the steroidal liposomes to be administered in vivo. For instance, when using cholesterol hemisuccinate, 2.5 to 700 μmoles of the tris-salt form may be added to 2.0 ml aqueous buffer containing Tris-HCl (tris(hydroxymethyl)aminomethane hydrochloride) in order to form vesicles; in this case the aqueous buffer should be essentially free of divalent or multivalent cations.

According to the present invention, the entrapment of water-soluble compounds, water-insoluble compounds, or sparingly soluble compounds in liposomes composed of the salt form of organic acid derivatives of sterols may be accomplished in a number of ways:

(1) A water-insoluble compound can be added to a suspension of sterol liposomes (either multilamellar sterol vesicles or unilamellar sterol vesicles), which were prepared as described above using an appropriate salt form of an organic acid derivative of a sterol. The compound is entrapped in the liposomes because it partitions into the sterol bilayers. This embodiment may be conveniently carried out as follows: the water-insoluble compound may be dissolved in an appropriate organic solvent which is then evaporated leaving a film or residue of the compound. When an aqueous suspension of previously formed sterol liposomes is added to the residue, the residue will be entrapped in the bilayers of the sterol liposomes.

(2) A water-insoluble compound and the salt form of an organic acid derivative of a sterol can both be cosolubilized in an organic solvent which is then evaporated off leaving a film comprising a homogeneous distribution of the water-insoluble compound and the sterol derivative. A suspension of multilamellar sterol vesicles containing the entrapped compound is formed with an aqueous phase is added to the film with shaking. The multilamellar vesicles may be converted to unilamellar vesicles as previously described.

(3) A water-soluble compound or a water-insoluble compound can be entrapped in the sterol liposomes by adding the compound to the aqueous phase which is used in the preparation of the sterol vesicles; i.e., the compound can be added to the aqueous phase before or simultaneously with the addition of the salt form of an organic acid derivative of a sterol. In this case, a water-insoluble compound becomes entrapped when it partitions into the bilayers during vesicle formation; whereas a water-soluble compound becomes entrapped in the aqueous compartment of the sterol vesicles during vesicle formation. In either case, the multilamellar vesicles can be converted to unilamellar vesicles as previously described.

(4) If the bioactive agent is ionizable, the free base of the bioactive agent may be used as the counterion to prepare the salt form of the organic acid derivative of a sterol. The sterol liposomes may be prepared by any of the methods previously described herein using the bioactive agent-salt form of the organic acid derivative of the sterol. For example, the free base of miconazole, an antifungal compound, may be used to make the salt derivatives in this embodiment of the present invention.

Using any of the four method described above, both a water-soluble compound and a water-insoluble compound may be entrapped in one sterol liposome preparation.

According to the methods described above for the entrapment of water-insoluble compounds using the sterol vesicles of the present invention, it is not required that the vesicles remain intact once a water-insoluble compound partitions into the bilayers. In fact, it is conceivable that once the compound partitions into the bilayers the vesicles will be disturbed or disrupted leading to the leakage or release of aqueous entrapped compounds.

According to one embodiment of the present invention, sterol liposomes are prepared using the tris-salt form of cholesterol hemisuccinate as follows: 4.5 to 200 mg of the tris-salt form of cholesterol hemisuccinate is added per ml or aqueous buffer containing 0.01 M Tris-HCl, 0.14 M NaCl. The mixture is shaken and a milky suspension of cholesterol hemisuccinate multilamellar vesicles forms. The vesicles may be pelleted by centrifugation and washed repeatedly with aqueous buffer. The suspension of cholesterol hemisuccinate multilamellar vesicles (CHS-MLVs) may be sonicated (e.g. in a bath-type sonicator) in order to form cholesterol hemisuccinate small unilamellar vesicles (CHS-SUVs). Alternatively, the CHS-MLVs may be passed through a French pressure cell (a French Press) at 40,000 psi or the CHS-MLVs may be passed through two 100 nm Nucleopore (TM) filters at 300–400 pa in order to form CHS-SUVs. The cholesterol hemisuccinate vesicles (whether MLVs or SUVs) are unstable in the presence of divalent cations; i.e. upon exposure to divalent cations the entrapped aqueous compartment and water-soluble compounds are released. Thus, the aqueous medium used in the preparation or during storage of the vesicles should be essentially free of divalent cations.

The compounds which are entrapped according to the method of the present invention may be used in various ways. For example, if the compound is a bioactive agent, the sterol liposome entrapped compound may be administered in vivo. This facilitates the in vivo delivery of bioactive agents which are normally insoluble or sparingly soluble in aqueous solutions. Entrapment in liposomes composed of the salt form of organic acid derivatives of sterols enables ease in the administration of such insoluble compounds at a higher dose:-volume ratio. In fact, the sterol vesicles of the present invention are particularly advantageously used in vivo because the vesicles may be used to entrap one or more bioactive agents for delivery in vivo. Furthermore, the vesicles of the present invention offer an advantage over conventional lipid vesicles or liposomes when used in vivo because they can be prepared without using organic solvents. The fate of the entrapped agent in vivo depends upon the route or mode of administration. For instance, when the sterol liposome entrapped agent is administered intravenously the clearance of the agent in vivo follows a pathway different from that of non-entrapped agent or that of an agent entrapped in conventional liposomes composed of phospholipids (i.e., MLVs, SUVs, REVs, LUVs). On the other hand, intramuscular administration of the sterol liposome entrapped agent results in a sustained release of the agent in vivo.

Virtually any bioactive agent can be entrapped within the sterol liposomes of the present invention. Such agents include but are not limited to antibacterial agents, antiviral agents, antifungal agents, anti-parasitic agents, tumoricidal agents, anti-metabolites, polypeptides, peptides, proteins, toxins, enzymes, hormones, neurotransmitters, glycoproteins, lipoproteins, immunoglobulins, immunomodulators, vasodilators, dyes, radiolabels, radio-opaque compounds, fluorescent compounds, receptor binding molecules, anti-inflammatories, antiglaucomic agents, mydriatic compounds, local anesthetics, narcotics, vitamins, nucleic acids, polynucleotides, etc. The entrapment of two or more compounds simultaneously may be especially desirable where such compounds produce complementary or synergistic effects.

The sterol liposome entrapped agent may be administered in vivo by any suitable route including but not limited to: inoculation or injection (e.g., intravenous, intraperitoneal, intramuscular, subcutaneous, intra-aural, intraarticular, intra-mammary, and the like), topical application (e.g., on areas such as eyes, skin, in ears or on afflictions such as wounds and burns), and by absorption through epithelial or mucocutaneous linings (e.g., nasal, oral, vaginal, rectal, gastrointestinal mucosa, and the like).

In another example of their use, the sterol liposome entrapped compound may be incorporated into a broad range of materials including but not limited to other lipid vesicles or liposomes, gels, oils, emulsions and the like. For instance, the suspension of sterol liposomes containing the entrapped compound may be added to the aqueous phase as an ingredient in any type of liposome preparation (e.g., phospholipid MLVs, SUVs, LUVs, REVs, and others). This allows for the entrapment of the compound in the phospholipid liposomes.

Other uses, depending upon the particular properties of a preparation, may be envisioned by those skilled in the art. For example, because of their divalent cation sensitivity, the cholesterol hemisuccinate liposomes of the present invention may be made to entrap indicator dyes which are sensitive to divalent cation sensitive for use in colorimetric diagnostic assays in vitro.

CHS-tris Antifungal Compositions

The tris(hydroxymethyl)aminomethane salt of cholesteryl hemisuccinate ("CHS-tris") forms a semi-solid gel when dissolved at a high concentration (for example, about 100 mg/ml or greater) in hot organic solvents such as ethanol and allowed to cool to about 25° C. The resulting gel is more uniform in appearance, if the hot solvent CHS-tris solution is sonicated briefly in a bath sonicator. The solvent in the gel can be removed by evaporation in air or under vacuum. The gel (before or after removal of the solvent) disperses as small vesicles, upon hydration.

Bioactive agents, for example, antifungal compounds can be incorporated into the gel, prior to gel formation, and the gel can then be administered intravaginally, intrarectally, topically, or orally. Antifungal compounds which may be present in the formulations of the instant invention include miconazole, terconazole, econazole, isoconazole, tioconazole, bifonazole, butaconazole, itraconazole, oxiconazole, fenticonazole, nystatin, naftifine, ketoconazole, ciclopirox olamine, clotrimazole, zinoconazole, amphotericin B, and the like. It is to be understood that free bases or pharmaceutically acceptable salts of the antifungal compounds are within the scope of the present invention. A pharmaceutically acceptable salt is one which is nontoxic and does not cause unacceptable side effects. Generally, any antifungal compound compatible with the formulations may be employed. Other ingredients can be added to the ethanol solution prior to gelling to give the final samples desirable physical characteristics such as softness, lubricity, stability, scent, taste and the like. Useful additional ingredients include waxes, vegetable butters such as either hard butter triglycerides of lauric acid derived from vegetable fats, or cocoa butter, and phospholipids such as egg phosphocholine. Organic carboxylic acids which are weak to moderately acidic such as lactic acid can be added to lower the pH and/or increase the solubility of basic drugs. Preferably the organic carboxylic acid has up to 12 carbon atoms, more preferably up to 6 carbon atoms. Improved solubility of polar, basic antifungals, such as terconazole in CHS-tris, occurs when about 5-15 percent by weight of an organic carboxylic acid, such as lactic acid, is present in the formulation. Certain compounds such as lactic acid may also be desirable due to their ability to hold water and therefore "soften" the formulation. The additional ingredients or excipients should be stable, pharmaceutically acceptable, i.e., nontoxic, should not adversely interfere with the efficacy and safety of the bioactive agent, and should be appropriate for the mode of administration, such as intravaginally.

Suppositories

The gel can be formed in any suitable container. For suppositories, the gels may be formed in molds of appropriate size and shape and administered in the form of an intravaginal suppository which will slowly "disperse" to form liposomes in vivo. The gel can also be hydrated prior to use to form a cream or suspension which are administered topically or intravaginally. The hydrated gels have been shown by x-ray diffraction to consist of multilamellar structures typical of liposomes. Alternatively, the gel can be formed as a cream or suspension by other methods known to those skilled in the art.

When making suppositories, CHS-tris gels are generally difficult to mold because of a lack of adhesion of the gel particles to each other. Therefore, a wax, a vegetable butter, phospholipid or other molding agent can be included. For hard butters such as Wecobee M, the weight-to-weight ratio of CHS-tris to hard butter is between about 0.15:1 and 4:1. Remington's Pharmaceutical Sciences, 16th Ed., Mack Publishing Co., Easton, PA, 1980, pages 1530-1533, discusses suppository formulations and is incorporated herein by reference.

For phospholipids such as egg phosphocholine, the weight-to-weight ratio of CHS-tris to phospholipid is between about 10:1 and 1:1. When phospholipids such as egg phosphocholine are employed, an organic carboxylic acid having, for example, 1-6 carbon atoms such as lactic acid can be added in order to increase the solubility of the antifungal agent if necessary. The amount of lactic acid added to an antifungal, such as miconazole or terconazole base, is preferably equimolar or less.

Waxes, vegetable butters, and the like are chosen which are compatible with the antifungal CHS-tris formulation, are solid at room temperature and melt at at body temperature. Phospholipids are chosen which are compatible with the antifungal CHS-tris formulations and disperse in the vaginal mucosa. Other carriers known in the art may also be employed for the intravaginal administration of the formulations of the present invention.

Creams

CHS-tris cream formulations of the present invention are prepared by dissolving CHS-tris in an organic solvent, preferably between about 50 and 100 mg of CHS-tris per ml of solvent. Useful solvents including alcohols, such as methanol, ethanol and isopropanol, are those in which the antifungal compound or other bioactive agent is soluble. The CHS-tris is added to boiling solvent which is then removed from the heat source. The bioactive agent is then added with gentle stirring. The resulting solution is poured into a large container so that there is considerable exposed surface area of the solution in order to facilitate solvent evaporation.

The solution is briefly sonicated for between about 30 and 180 seconds until gelling begins. The terms "gel" and "gelling" refer to a viscous composition which resembles jelly or gelatin in its texture. The colloidal properties of the viscous composition are not known. The container is covered tightly and gelling is completed at about 20°-30° C., preferable 25° C. in about four hours. The cover is removed and the solvent is allowed to evaporate. The solvent can also be removed in vacuo.

The resulting dry gel is solid and can be cut into sections and ground in a blender with frozen carbon dioxide until a fine, granular powder is obtained. The powder is mixed with water until a homogeneous cream having the desired volume is obtained. The consistency of the cream is dependent upon the amount of water added. In general, if the final concentration of CHS-tris is less than about 200 mg/ml, the resulting composition is fluid and could be administered as a douche. Alternatively, a cream can be produced by the addition of waxes and the like which increase the viscosity of the composition. If the concentration is about 200-400 mg/ml, the resulting composition can be administered as a cream. If the concentration is greater than about 450 mg/ml, the resulting composition will be a semi-solid to solid gel that could be administered as a suppository.

Administration

CHS-tris formulations of the present invention which contain antifungal agents such as miconazole, terconazole and the like are useful for treating vaginal infections such as those caused by *Candida*, for example, *Candida albicans*, in mammals including humans. Infections in other parts of the body such as thrush can also be treated using formulations of the present invention. These formulations are conveniently administered intravaginally as douches, creams or suppositories. The amount of antifungal agent in douche, cream or suppository dosage forms will depend on several factors for example, the potency of the drug, irritation caused by the drug, how quickly the drug is washed out of the vaginal cavity by normal vaginal secretions, etc. but can range from about 10 to 1500 mg. For example, about 50 mg to 1.2 g for miconazole, or about 20 mg to 480 mg for terconazole are useful doses. This amount of drug can be incorporated in a suppository generally weighing about 3 grams or less or in a cream dose of about 5 ml or less. In general, a more concentrated formulation administered in a smaller volume is more desirable from the standpoint of convenience and comfort of the patient.

Often, only one administration of the formulation of the present invention is necessary to cure a vaginal infection susceptible to the antifungal agent. For prior art formulation, generally three to six to as many as fourteen doses are required.

CHS-tris Peptide Compositions

Proteins and other peptides, especially those which are hydrophobic such as growth hormones, insulin, low density lipoproteins and the like, can be included in formulations of the present invention in order to solubilize, control the rate of release or target the site of action. The peptides are generally administered parenterally, such as intravenously, intramuscularly or intraperitoneally. Growth hormones which can be employed includes human growth hormone, bovine growth hormone and porcine growth hormone. For example, bovine growth hormone can be solubilized in aqueous buffer using CHS-tris. Between about 5 and 170 mg or more, preferably 150–170 mg, of bovine growth hormone per ml of aqueous buffer can be solubilized with CHS-tris, preferably between about 5 and 300 mg of CHS-tris and more preferably between about 25 and 50 mg of CHS-tris per ml of aqueous buffer.

One method of solubilizing proteins and other peptides using CHS-tris is to prepare a multilamellar liposome (MLV) in aqueous buffer. The resulting MLV's can be used as is or sonicated to obtain SUV's. The peptide is suspended in the aqueous buffer-liposome mixture and partitions into the liposomal bilayers, thereby being solubilized. Alternatively, the solubilized peptide can be employed as the aqueous phase in preparing SPLV's. The resulting solubilized peptide composition can be administered to a mammal, including humans.

Growth hormones can be employed to increase milk production or to increase or initiate growth. For administration of bovine growth hormone to dairy cows to increase milk productions intermuscularly, generally about 10 mg per day is required. For a 30 day controlled release dosage form of the present invention about 300 to 1200 mg are administered as a single dose.

For controlled release dosage forms of peptides, the amount administered is determined by a veterinarian or physician, as appropriate. The release characteristics of the dosage form, the amount of peptide which can be utilized by the body, toxicological consideration, and the like will determine the actual dose.

The following examples are given for purposes of illustration and not by way of limiting the scope of the invention.

Example: Cholesterol Hemisuccinate Liposomes Entrapping Water-Soluble Compounds

The following subsections describe the preparation of cholesterol hemisuccinate vesicles which entrap arsenazo III, inulin or chromium. Parameters such as the encapsulation efficiency and the captured volume are assessed; the calcium dependent instability of the cholesterol vesicles is demonstrated. Freeze-etch electron microscopy, X-ray diffraction and electron spin resonance of the cholesterol hemisuccinate vesicles are also described.

Lipsomes Prepared Using Various Salt Forms of Cholesterol Hemisuccinate

The following subsections describe the preparation of CHS liposomes using various salt forms of cholesterol hemisuccinate.

In all examples involving the tris-salt form of cholesterol hemisuccinate (hereinafter referred to as tris-salt CHS) the tris-salt CHS was either purchased from Sigma Biochemicals, St. Louis, MO, and used without purification or synthesized as follows: 30 ml of a 3.3 molar solution of Tris base was added to 1.5 liters of a 67 M molar solution of cholesterol hydrogen succinate (ICN, Cleveland, OH) in ether. The resulting solution was rotoevaporated to a wet residue and lyophilized for 12 hours. The resulting tris-salt CHS was recrystallized three times from ethyl acetate. Residual ethyl acetate was removed by heating to 56° C. under vacuum (0.1 mm Hg).

6.1.1. Tris-Salt Cholesterol Hemisuccinate-MLVs

Tris-salt CHS (54 mg) was added to a 1 ml solution of arsenazo III (4.5 mM, final concentration) in 0.01 M Tris-HCl (pH 7.3), 0.14 M NaCl. A milky suspension of CHS-MLVs was formed by mechanical shaking. The CHS-MLVs were pelleted by centrifugation at 10,000 $\times$ g for 15 minutes, and the resulting pellet was washed three times using 10 ml 0.01 M Tris-HCl (pH 7.3), 0.14 M NaCl. The resulting pellet was red in color indicating entrapment of the arsenazo III.

6.1.2. 2-Amino-2-Methyl-1,3-Propanediol Cholesterol Hemisuccinate-MLVs

The 2-amino-2-methyl-1,3-propanediol salt of cholesterol hemisuccinate (50 mg) was added to a 1 ml solution of arsenazo III (4.5 mM, final concentration) in 0.01 M 2-amino-2-methyl-1,3-propanediol-HCl (pH 7.3), 0.07 M KCl, 0.07 M NaCl. The suspension of CHS-MLVs was formed by mixing vortically with glass beads. The CHS-MLVs were pelleted by centrifugation at 10,000 $\times$ g for 15 minutes, and the resulting pellet was washed three times as described in Section 6.1.1. The resulting pellet was red in color indicating entrapment of the arsenazo III.

6.1.3 2-Aminoethanol Cholesterol Hemisuccinate-MLVs

The 2-aminoethanol salt of cholesterol hemisuccinate (50 mg) was added to a 1 ml solution of arsenazo III (4.5 mM, final concentration) in 0.01 M 2-aminoethanol-HCl (pH 7.3), 0.07 M KCl, 0.07 M NaCl. The suspension of CHS-MLVs was formed by mixing vortically with glass beads. The CHS-MLVs were pelleted by centrifugation at 10,000 $\times$ g for 15 minutes, and the resulting pellet was washed three times as described in Section 6.1.1. The resulting pellet was red in color indicating entrapment of the arsenazo III.

6.1.4. Bis-Tris-Propane Cholesterol Hemisuccinate-MLVs

The bis-tris-propane salt of cholesterol hemisuccinate (50 mg) was added to a 1 ml solution of arsenazo III (4.5 mM, final concentration) in 0.01 M bis-tris-propane-HCl (pH 7.3), 0.07 M KCl, 0.07 M NaCl. The suspension of CHS-MLVs was formed by mixing vortically with glass beads. The CHS-MLVs were pelleted by centrifugation at 10,000 $\times$ g for 15 minutes, and the resulting pellet was washed three times as described in Section 6.1.1. The resulting pellet was red in color indicating entrapment of the arsenazo III.

6.1.5. Triethanolamine Cholesterol Hemisuccinate-MLVs

The triethanolamine salt of cholesterol hemisuccinate (50 mg) was added to a 1 ml solution of arsenazo III (4.5 mM, final concentration) in 0.01 M triethanolamine-HCL (pH 7.3), 0.07 M KCl, 0.07 M NaCl. The suspension of CHS-MLVs was formed by mixing vortically with glass beads. The CHS-MLVs were pelleted by centrifugation at 10,000 $\times$ g for 15 minutes, and the resulting pellet was washed three times as described in Section 6.1.1. The resulting pellet was red in color indicating entrapment of the arsenazo III.

6.1.6. Miconazole Cholesterol Hemisuccinate-MLVs

The free base of miconazole was prepared as follows: an aqueous solution of NaOH was titrated into a suspension of miconazole-nitrate in ether. The ether phase was collected and the ether was evaporated leaving an oil comprising the miconazole free base. The oil was then added to ethanol containing cholesterol hydrogen succinate. The ethanol was evaporated leaving a film comprising the salt form of miconazole cholesterol hemisuccinate. Then a saline solution was added to the film. After extensive vortical mixing, vesicles were observed in the solution.

6.1.7. Cholesterol Hemisuccinate-SUVs Prepared By Sonication

CHS-MLVS were prepared as described in Sections 6.1.1., 6.1.2., 6.1.3., 6.1.4., and 6.1.5., except that the arsenazo III was omitted. Each final pellet of vesicles was resuspended in 2 ml of the buffer in which it was prepared and sonicated in a bath sonicator until the milky suspension turned clear indicating the conversion of CHS-MLVs to CHS-SUVs.

6.1.8. Cholesterol Hemisuccinate-SUVs Prepared By Extrusion Techniques

CHS was dispersed in 10 mM HEPES, 150 mM NaCl (pH 7.5) at a concentration of 100 mg/ml. This material was extruded 10 times through a 30 nm Nucleopore polycarbonate filter resulting in CHS-SUVs.

6.1.9 Miconazole - CHS-Tris Cream

The tris(hydroxymethyl)aminomethane ("tris") salt of cholesterylhemisuccinate ("CHS-tris") (20.64 g), available from Sigma Chemical Co., St. Louis, MO, was dissolved in 206 ml of boiling ethanol. When the ethanol-CHS-tris solution was clear, it was removed from the heat and 5.16 grams of miconazole base in 103 ml ethanol was added with gentle stirring. The clear solution was poured into a large, flat dish (243×243×18 mm) and sonicated briefly in a large bath sonicator until gelling began. The dish was then covered tightly and allowed to complete gelling at 25° C. for four hours. The cover was removed and the ethanol allowed to evaporate. The dried gel was then cut into sections, placed in a blender with frozen carbon dioxide and ground until it was a fine, granular powder. The resulting powder was mixed with sterile, distilled water until a homogeneous cream with a final volume of 51.6 ml was obtained with a concentration of miconazole of 100 mg/ml.

The procedure was repeated using 10.32 g of miconazole to obtain a cream having a concentration of miconazole of 200 mg/ml.

Additional miconazole-CHS-tris formulations were prepared according to the above described procedures and materials with the materials having the proportions as follows:

| Miconazole (mg) | CHS-tris (mg) | Water (mg) |
|---|---|---|
| 50 | 100 | 850 |
| 100 | 200 | 700 |
| 100 | 400 | 400 |
| 200 | 400 | 500 |

6.1.10 Terconazole CHS-Tris Cream

CHS-tris (2.0 g) was dissolved in 20 ml of boiling ethanol. When the ethanol-CHS-tris solution was clear, it was removed from the heat and 1.0 gm of terconazole (in 50 ml of ethanol) and 83 mg of L (+)- lactic acid (in 2 ml ethanol) was added with gentle stirring. The clear solution was poured into a large beaker and sonicated until "gelling" began. The beaker was covered tightly and allowed to complete gelling at room temperature for four hours. The cover was removed and the ethanol allowed to evaporate in air at 25° C. The dried gel was cut into sections, placed in a blender with frozen carbon dioxide and ground until it was a fine granular powder. This powder was mixed with 10 ml of water containing 6.3 g CHS-tris sonicated vesicles. The resulting suspension was mixed with distilled, sterile water until a homogeneous cream with a final volume of 20.8 ml was obtained having 48 mg terconazole per ml of cream.

6.1.11 Miconazole - CHS-Tris Suppository

CHS-tris (400 mg) was dissolved in 4 ml of boiling ethanol. 100 mg miconazole base in 1 ml ethanol and 1.2 g of a melted hard butter triglyceride of lactic acid derived from vegetable fats (Wecobee M, PVO International, Boonton, NJ), was added with gentle stirring. The resulting clear solution was aliquotted into 1.5 ml polypropylene microfuge tubes, sonicated briefly (approximately 60 second) to "gel" the CHS-tris and left at room temperature for four hours to solidify completely. The polypropylene "mold" was removed and the semi-solid gels were put in a vacuum dessicator overnight to remove the residual ethanol.

Other miconazole CHS-tris suppository formulations prepared according to the above described procedure are listed below.

| Miconazole (mg) | CHS-tris (mg) | Wecobee M (mg) | Lactic Acid (mg) | Egg Phosphocholine (mg) |
|---|---|---|---|---|
| 3.4 | 6.8 | 80.3 | | |
| 3.4 | 13.6 | 20.5 | | |
| 6.9 | 13.8 | 80.3 | | |
| 6.9 | 27.6 | 44.0 | | |
| 10.3 | 20.6 | 80.3 | | |
| 20.0 | 41.0 | 12.0 | | |
| 20.6 | 41.2 | | | |
| 20.6 | 41.2 | | 2.2 | 10.3 |
| 20.6 | 41.2 | 79.4 | | |

6.1.12 In Vivo Activity For Vaginal Candida Infections

Ovariectomized rats (Charles River Breeding Laboratories) were treated weekly with beta-estradiol valerate to induce a state of constant estrus (and susceptibility to vaginal Candida infection). The rats were inoculated, intravaginally with $5 \times 10^6$ CFU of *Candida albicans*. Starting on the third day after inoculation, infected rats were treated, intravaginally, with 2% weight to volume miconazole nitrate cream twice a day for three days, 12% miconazole nitrate cream administered once on the third day post-inoculation, or with one of the CHS-tris suppository or cream preparations of the present invention administered only once on the third day post-inoculation. Some rats received no treatment. On the sixth or tenth day after inoculation, the vaginas of all rats were sampled for *Candida albicans*. Those rats with fewer than 25 CFU/vaginal swab were considered cured.

6.2. Entrapment of Inulin in Cholesterol Hemisuccinate MLVs

Cholesterol hemisuccinate multilamellar vesicles(CHS-MLVs) incorporating $^3$H-Inulin as the entrapped agent were prepared as follows: $^3$H-Inulin (1.0 mCi/ml, New England Nuclear, Boston, MA) was dissolved in 2 ml 0.01 M Tris-HCl (pH 7.3), 0.14 M NaCl. Then 40 mg of tris-salt CHS was added to the solution and the resulting mixture was mechanically dispersed by shaking. A milky suspension formed indicating the formation of multilamellar vesicles. The suspension was allowed to stand undisturbed for 2 hours at which time the suspension was diluted to a final volume of 10 ml using 0.01 M Tris-HCl (pH 7.3), 0.14 M NaCl. The radioactivity of a 10 μl aliquot was determined to be 24,625 cpm/10 μl by adding the aliquot to 10 ml scintillation fluid (40 g Omnifluor (New England Nuclear, Boston, MA) 6 l toluene, 4 l ethylene glycol monoethyl ether) and assaying radioactivity using a Beckmann L6800 liquid scintillation counter with windows set at 0.400. Radioactivity in counts per minute (cpm) was converted to disintegrations per minute (dpm) by applying the H# method of quench correction (Horrock, D. L. The Number Concept, Beckman Instruments, 1977). The CHS-MLVs were then pelleted by centrifugation at 10,000×g for 15 minutes. The resulting pellet was washed three times by resuspending the pellet in 10 ml 0.01 M Tris-HCl (pH 7.3), 0.14 M NaCl and repelletting by centrifugation at 10,000×g for 15 minutes. The washed pellet of vesicles was resuspended in 0.01 M Tris-HCl (pH 7.3), 0.14 M NaCl to a final volume of 10 ml; the radioactivity of a 10 μl aliquot was determined to be 3,442 cpm/10 μl. Therefore, a total of approximately 14% of the starting $^3$H-Inulin was entrapped in the CHS-MLVs.

6.2.1. Encapsulation Efficiency of Inulin in Cholesterol Hemisuccinate-MLVs and Egg Phosphatidylcholine-MLVs The encapsulation efficiencies of inulin entrapped in MLVs comprising varying concentrations of cholesterol hemisuccinate were compared to encapsulation efficiencies of inulin entrapped in MLVs comprising varying concentrations of egg phosphatidylcholine. (N.B., encapsulation efficiency for any liposome is defined as the fraction of aqueous compartment sequestered by bilayers; and is expressed as a percentage, see Section 2.1 supra.)

Multilamellar vesicles composed of either egg phosphatidylcholine (EPC) or tris-salt CHS were prepared using identical protocols in order to compare encapsulation efficiencies. Accordingly, tris-salt CHS at a concentration of 40, 80, 160, 320 or 400 mg in 2.0 ml 0.01 M Tris-HCl (pH 7.3), 0.14 M NaCL buffer with 5 μl H-inulin (217.0 mCi/mg) was mixed vortically and allowed to stand for 2 hours, forming CHS-MLVs with $^3$H-inulin as the entrapped compound. An additional 3 ml 0.01 M Tris-HCl (pH 7.3), 0.14 M NaCl buffer was added to the suspension which was left at room temperature overnight. Then, approximately 3.0 ml 0.01 M Tris-HCl (pH 7.3), 0.14 M NaCl buffer was added to bring the total volume up to 10 ml.

Multilamellar vesicles composed of egg phosphatidylcholine (EPC-MLVs) (Avanti, Birmingham, AL) were prepared according to the following protocol: 40, 80, 160, 320 or 400 mg/ml EPC was suspended in sufficient chloroform to completely dissolve the phospholipid. The chloroform was evaporated to dryness leaving a waxy deposit on the test tube. Then 2.0 ml of 0.01 M Tris-HCl (pH 7.3), 0.14 M NaCl buffer with 5 μl $^3$H-Inulin (217.0 mCi/mg) was added, the mixture allowed to "swell", and the resulting EPC-MLVs were dispersed by extensive vortical mixing. An additional 3 ml 0.01 M Tris-HCl (pH 7.3), 0.14 M NaCl buffer was added to the suspension which was left at room temperature overnight. Then, the mixture was brought up to a total volume of 10 ml with 0.01 M Tris-HCl (pH 7.3), 0.14 M NaCl buffer.

The encapsulation efficiency of $^3$H-inulin by the CHS-MLVs and EPC-MLVs was determined as follows: The radioactivity in the 20 μl aliquot of each initial mixture of ingredients was determined by scintillation counting as previously described. After formation, the liposomes were pelleted by centrifuging the suspension for 10-20 minutes at 10,000×g, each pellet was washed four times in 10 ml 0.01 M Tris-HCl (pH 7.3), 0.14 M NaCl buffer, and resuspended to a final volume of 10 ml 0.01 M Tris-HCl (pH 7.3), 0.14 M NaCl buffer. The radioactivity of a 20 μl aliquot of this final washed sample was determined. The fraction of the initial radioactivity measured in this final sample represented the $^3$H-inulin entrapped in the lipid vesicles.

As illustrated in Table I, an increase in encapsulation efficiency is proportional to an increase in CHS concentration but, more importantly, CHS-MLVs made using 20-200 mg/ml CHS demonstrate a higher encapsulation efficiency for inulin than do EPC-MLVs made using the same concentration of phospholipid.

TABLE I
COMPARISON OF ENCAPSULATION EFFICIENCIES OF INULIN IN PHOSPHOLIPID VESICLES AND CHOLESTEROL HEMISUCCINATE VESICLES

| Concentration of Lipid (mg/ml) | % $^3$H—Inulin Entrapped | |
|---|---|---|
| | EPC-MLVs[a] | CHS-MLVs[b] |
| 20 | 2 | 10 |
| 40 | 4 | 14 |
| 80 | 5 | 29 |
| 160 | 8 | 38 |
| 200 | 11 | 60 |

[a]Egg phosphatidylcholine multilamellar vesicles.
[b]Cholesterol hemisuccinate multilamellar vesicles.

In order to determine whether the encapsulation efficiency of CHS-MLVs was influenced by the amount of time the CHS was in contact with free $^3$H-Inulin in aqueous buffer, CHS-MLVs were prepared as follows: either 80 or 300 mg tris-salt CHS was mixed vortically in 20 ml 0.01 M Tris-HCl, 0.14 M NaCl buffer containing 10 μl $^3$H-Inulin (217 mCi/mg specific radioactivity), thus forming CHS-MLVs using a concentration of 40 and 150 mg/ml CHS respectively.

Five samples at each of the two lipid concentrations were prepared and the CHS-MLV suspensions were allowed to stand at room temperature in the 2.0 ml of 0.01 M Tris-HCl (pH 7.3), 0.14 M NaCl buffer. At the following time intervals: 0, 15, 30, 60, and 120 minutes, the samples were brought up to 10 ml with the same buffer. An initial 10 μl aliquot of each sample was removed for scintillation counting as previously described. The samples were then centrifuged at 10,000×g for 10 minutes, and each pellet was washed four times in 10 ml buffer. The final pellet was suspended in buffer to a final volume of 10 ml, and the radioactivity of a 10 μl aliquot of each final sample was compared to that of the initial sample at each time point. The results demonstrated no significant difference in encapsulation efficiency for the five time points for either concentration of lipid tested. This indicates that entrapment of about 12% or 20% of the initial $^3$H-Inulin added to the preparation occurred regardless of contact time at 40 or 150 mg/ml CHS respectively. This demonstrates that unlike conventional MLVs prepared using egg phosphatidylcholine, no "swelling time" is required in the preparation of CHS-MLVs.

6.3. Entrapment of Inulin in Cholesterol Hemisuccinate-SUVs

Small unilamellar vesicles composed of cholesterol hemisuccinate (CHS-SUVs) containing $^3$H-Inulin as the entrapped agent were prepared as follows: 100 μl of 1.0 mCi/ml ³H-Inulin (New England Nuclear, Boston Mass.) was dissolved in 2.5 ml 0.01M Tris-HCl (pH 7.3), 0.14M NaCl to which either 100 or 200 mg tris-salt CHS was added. After mixing vortically with glass beads, the mixture was drawn off from the beads in the pipette, and sonicated to clarity, i.e. for approximately 2 hours. Clearing of the suspension indicates a transition of CHS-MLVs to small unilamellar vesicles. The final concentrations of CHS in the CHS-SUV suspensions was 40 mg/ml and 80 mg/ml, respectively.

In order to demonstrate inulin entrapment (see Section 5 supra), the CHS-SUVs were separated from unentrapped inulin by gel filtration as follows: each liposome suspension was applied separately to a Bio-Gel A-15m, 100–200 mesh agarose column (Bio-Rad Laboratories, Richmond, Calif.) with an operating range of 40,000 to 15,000,000 daltons molecular weight, equilibrated and calibrated with 0.01M Tris-HCl (pH 7.3), 0.14M NaCl buffer. Then, 1 ml fractions which eluted from the column were collected and the radioactivity of a 10 μl aliquot of each fraction was determined as previously described. A clear separation of free from sequestered inulin was obtained by the gel filtration thus indicating the entrapment of the inulin in the CHS-SUVs. This analysis indicated that about 1% of the inulin was entrapped in the CHS-SUVs.

6.4. Entrapment of Chromium in Cholesterol Hemisuccinate MLVs

Cholesterol hemisuccinate multilamellar vesicles incorporating ⁵¹Chromium as the entrapped agent were prepared as follows: 15.0, 40.0, 65.8, 100.0, 175.0, 263.2, 526.4 or 658.0 μmoles of tris-salt CHS was added to 5 ml 0.01M Tris-HCl, 0.14M NaCl, pH 7.3, containing trace amounts of ⁵¹Chromium New England Nuclear, Boston, Mass.) and allowed to stand at room temperature for 2 hours, resulting in a suspension of CHS-MLVs containing ⁵¹Chromium entrapped.

6.4.1. Encapsulation Efficiency of Chromium in Cholesterol Hemissuccinate-MLVs In order to determine the encapsulation efficiency of the CHS-MLVs prepared in Section 6.4 samples of each preparation were pipetted into dialysis bags (Thomas Scientific, Catalog No. 3787-D22, molecular weight cut off of 12,000 daltons) that had been boiled three times in distilled water. The samples in the dialysis bags were initially counted in a gamma counter (TmAnalytic, model no. 1191). The samples were then dialyzed for 20 hours against the same 0.01M Tris-HCl, 0.14M NaCl pH 7.3, buffer in retentate:dialysate ratios of greater than 1:150, respectively; the dialysate was changed every 2 hours for the first 6 hours. Encapsulation efficiency was determined by computing the percentage of initial counts retained.

As indicated in Table II, an increase in encapsulation efficiency is proportional to an increase in CHS concentration.

TABLE II

ENCAPSULATION EFFICIENCY OF CHROMIUM IN CHOLESTEROL HEMISUCCINATE VESICLES

| Concentration of CHS (μmol) | % ⁵¹Chromium Entrapped |
|---|---|
| 15.0 | 14.79 |
| 40.0 | 15.20 |
| 65.8 | 15.09 |
| 100.0 | 16.10 |
| 165.0 | 20.13 |
| 263.2 | 27.90 |

TABLE II-continued

ENCAPSULATION EFFICIENCY OF CHROMIUM IN CHOLESTEROL HEMISUCCINATE VESICLES

| Concentration of CHS (μmol) | % ⁵¹Chromium Entrapped |
|---|---|
| 526.4 | 40.74 |
| 658.0 | 48.03 |

6.4.2. Captured Volume in Cholesterol Hemisuccinate-MLVs: Chromium Entrapment and Cholesterol Hemisuccinate Concentration The captured volume of the CHS vesicles prepared as described in Section 6.4.1. was determined for each concentration of cholesterol hemisuccinate by computing the captured solute using the following calculation:

$$\frac{\% \text{ entrapment} \times \text{initial aqueous volume}}{\mu\text{mol CHS}}$$

The data illustrated in FIG. 1 indicate that less chromium/mole of lipid is entrapped as the concentration of tris-salt CHS is increased. Thus, although an increase in the encapsulation efficiency is proportional to the increase in lipid concentration, the captured solute decreases as the lipid concentration increases. The number of trials per point are indicated in parenthesis next to each point.

6.5. Ultrastructure of Cholesterol Hemisuccinate Liposomes

Samples of CHS-MLVs and CHS-SUVs, prepared using the tris-salt of cholesterol hemisuccinate as described in Section 6.1. except that the inulin was omitted, were prepared for freeze-etch electron microscopy (for freeze-etch method See Pfenninger et al., 1975, J. Cell Biol. 65: 15–28).

Electron microscopy of the CHS-MLV freeze-etched preparation revealed discrete units bounded by at lease one lamella, i.e., liposomes or lipid vesicles. There was a vast heterogeneity of size of the CHS-MLVs, ranging from 800 to 10,000 nm in diameter.

The larger vesicles could be categorized into a number of classes including: those with one or a few outer lamellae, and those with many lamellae. Most of the larger vesicles had substantial areas inside with a grainy appearance, possibly indicating the aqueous chambers. In many instances, small vesicles or groups of small vesicles were apparent, more or less free inside the larger vesicles, sometimes four or five layers deep. This apparent "nesting" is commonly observed in conventional liposomes made with a negatively charged phospholipid.

Occasionally, zones of closely apposed lamellae could be seen. These appear similar in all respects to the lamellae of conventional phospholipid MLVs.

The sonicated samples examined also contained many small spheroids ranging from 50 nm to 500 nm. These vesicles probably compare to SUVs made by sonication of phospholipid MLVs. As the smaller CHS-vesicles did not cleave, it was impossible to discern the structure of the interior or their component lamellae.

The CHS vesicles which were extruded through the 30 nm filter (10 times) vesicles with an average size of about 65 nm were observed. This contrasts with CHS vesicles prepared by the French press procedure which were extremely small (average diameter of 25 nm or less).

6.6. X-ray Diffraction Analysis of Cholesterol Hemisuccinate Liposomes

X-ray diffraction of various CHS-MLV preparations was performed using the 2-dimensional image-intensified X-ray detector apparatus described elsewhere (Gruner, S. M. 1977, PhD thesis, Princeton University, Princeton N.J. 09540 U.S.A.; Reynolds, Geo. T., Milch, J. R. and Gruner, S. M., 1978, Rev. Sci. Instr. 49:1241–1249; Tilcock, C. P. T., Bally, M. B., Farren, S. B., Cullis, P. R. and Gruner, S. M., 1984, Biochem, 23:2696–2703). X-ray repeat spacings are expressed as ± 0.5 Å. CHS dispersions were held in 1.5 mm glass X-ray capillaries sealed with epoxy plugs. Specimens were hydrated either gently or vigorously. For gentle hydration, the buffer was layered via a syringe onto dry CHS in the bottom of the X-ray capillary. The capillary was then momentarily centrifuged in a table top centrifuge to eliminate air bubbles from the lipid water paste. The capillaries were then sealed and allowed to equilibrate for at least 4 hours at 5° C. Vigorous hydration was accomplished by vortexing dry CHS with buffer and two glass mixing beads in a test tube. An aliquot was then transfered to an X-ray capillary.

Figure 2:
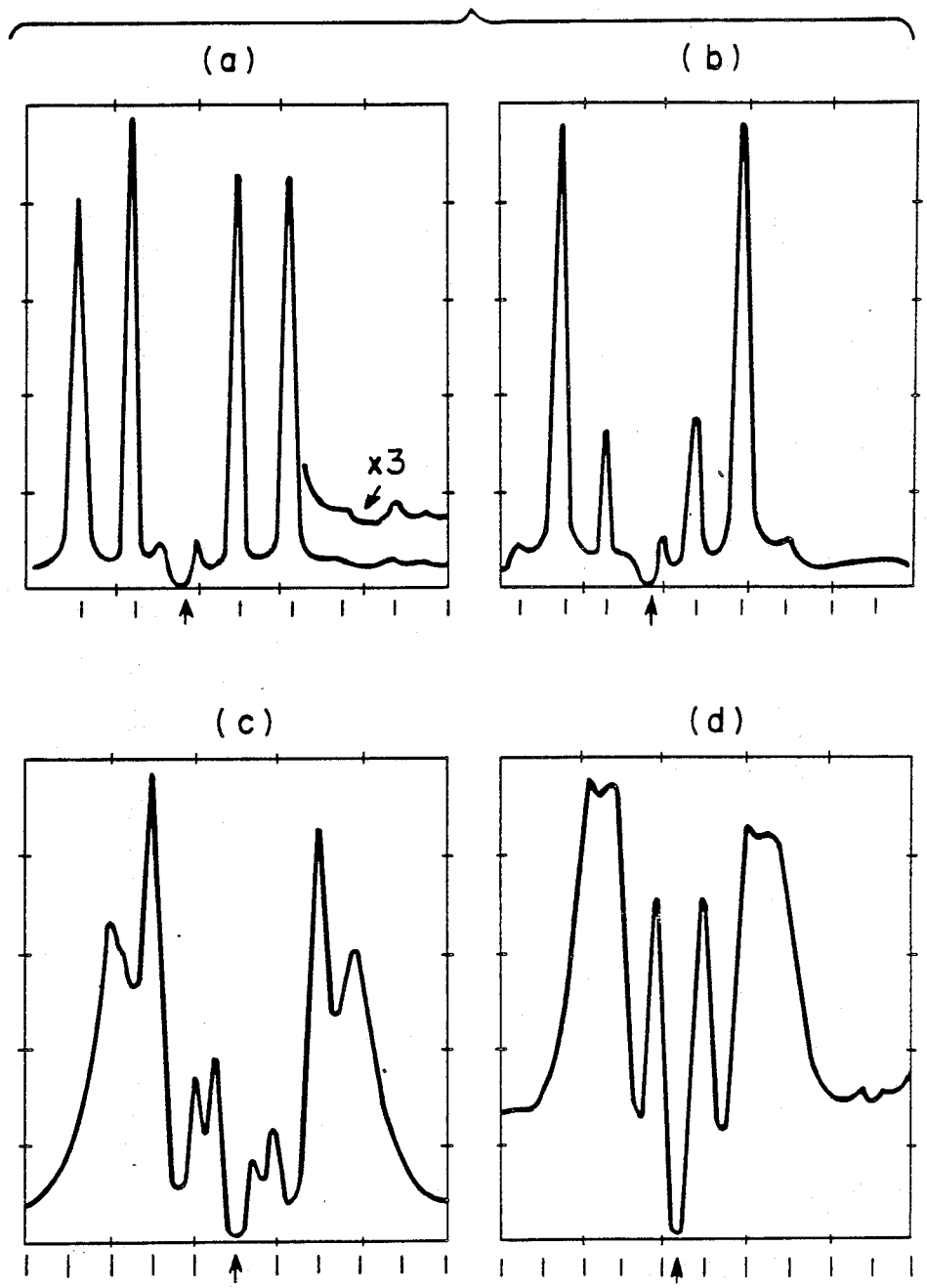
FIG. 2 represents the X-ray diffraction patterns obtained for four different CHS-MLV preparations.

X-ray diffraction demonstrated that hydrated CHS forms multilamellar structures. FIG. 2a and 2b show the low angle diffraction which resulted from gently hydrated specimens composed of 68.9% and 59.1%, CHS, respectively, by weight. Up to four equally spaced orders of diffraction are visible, consistent with multilamellar arrays of 68.1 Å and 79.8 Å, repeats, respectively. The orders were sharp and well resolved, indicating that the lattice contained very little disorder. These concentrated CHS specimens were of a uniform paste-like appearance with no visible excess buffer, consistent with the fact that the repeat specing increased as the aqueous content increased. At very high aqueous concentrations, gently hydrated CHS specimens exhibited a clearly visible pool of excess buffer solution on top of the hydrated lipid. The diffraction from such a sample (20.2% CHS by total weight) is shown in FIG. 2c. The broadening of the higher angle diffraction peaks is indicative of considerable disorder in the lattice. The disorder in the lattice made a definitive lattice assignment difficult, but if a lamellar fit was made, as indicated in FIG. 2c, the repeat was about 86 Å, suggestive of large aqueous spaces between the lipid bilayers.

If, instead of using gentle hydration, a 20.7% CHS specimen was prepared by mixing the dry lipid vortically with the buffer, then the specimen which resulted had a uniform milky appearance. As shown in FIG. 2d, the low angle diffraction exhibited a broad band of scatter with little evidence of a sharply defined lattice. A similar diffraction signature would be expected from a multilamellar system in which the interlamellar aqueous width varied widely. The x-ray diffraction of the dilute CHS dispersions is most consistently interpreted as arising from a multilamellar system in which the interlamellar forces are weak. For other lipid systems, such as dilute egg phosphatidylcholine dispersions, the x-ray diffraction pattern indicates a sharply defined lamellar lattice which is, by weight, mostly lipid (Rand, 1981 Annu. Rev. Biophys. Bioeng. 10:277–314). This well-defined lattice repeat is a result of a relatively sharp minimum in the lattice potential as a function of the lipid layer separation. If the potential vs. distance curve has only a shallow well, then one expects weak interlamellar forces and considerable lattice disorder. This appears to be the case with CHS vesicles.

The specimen of FIG. 2d has about an 86 Å repeat, as compared to the 68.1 Å repeat of FIG. 2a. This indicates that in the presence of excess buffer, CHS liposomes have a large water to lipid ratio. Similar results are observed with other charged lipid systems (Rand, 1981 supra).

6.7. Electron Spin Resonance Analysis of Cholesterol Hemisuccinate Liposomes Multilamellar liposomes made of egg phosphatidylcholine (EPC) (Avanti Polar Lipids, Birmingham, Ala.) were spin labelled and compared to similarly labeled tris-salt CHS-MLVs prepared essentially as described previously. In the case of EPC MLVs, 1 mole percent of either 5, 7, 9, 10, 12 or 16 doxylstearate (Molecular Probes, Junction City, Oreg.) was added to 40 mg lipid in chloroform and the resulting solution dried to a thin film by rotary evaporation. Then 2 ml of Tris-HCl buffer was used to hydrate this film by vortexing until the film was completely suspended. The resulting EPC-MLVs were washed twice prior to spectroscopy.

In the case of CHS-MLVs, 1 mole % of the appropriate spin label in ethanol was dried to a thin film on the side of a test tube to which was added 40 mg of tris-salt CHS powder and 2 ml of Tris-HCl buffer. This suspension was vortexed and the resulting liposomes washed twice. All electron spin resonance experiments were carried out with an IBM Instruments ER100D ESR spectrometer. The order parameter (S) was calculated as described elsewhere (Griffith and Jist in, Spin Labelling, Berliner, L. J. (ed.), Academic Press, N.Y. 1976).

Figure 3:
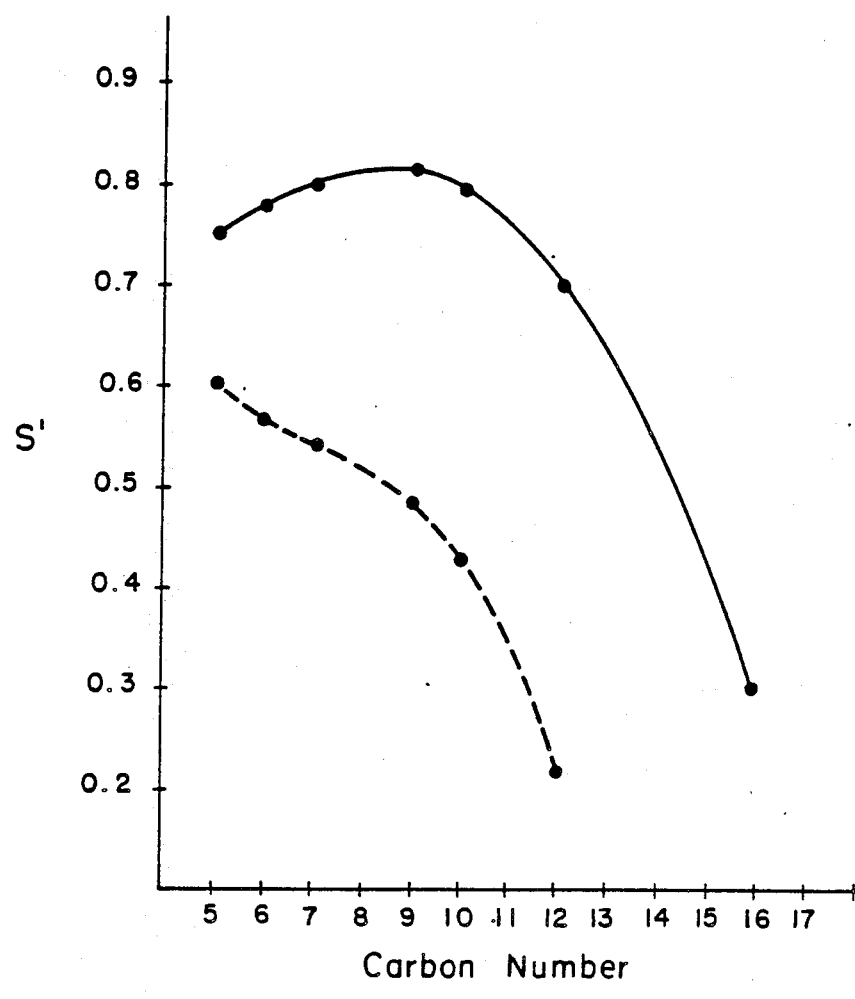
FIG. 3 represents the electron spin resonance data for CHS-multilamellar vesicles and EPC-multilamellar vesicles.

FIG. 3 shows the order parameter profiles of CHS-MLVs and EPC-MLVs as determined by spin labelling these preparations with either 5, 6, 7, 9, 10, 12 or 16 doxylsterate. For EPC bilayers, the order parameter decreases with increasing carbon number into the bilayer, as has been previously reported. The supramolecular structure of CHS bilayers is markedly different: not only is the bilayer dramatically more rigid than the EPC bilayer, but CHS systems actually exhibit an increase in order from the 50th to the 90th carbon, indicative of an entirely different physical and chemical bilayer structure than has previously been reported.

6.8. Isotonic Swelling of Cholesterol Hemisuccinate Liposomes

In the following series of experiments the isotonic swelling behavior of cholesterol hemisuccinate and phospholipid multilamellar vesicles was compared:

(1) CHS-MLVs were prepared as described in Section 6.1. using 40 mg tris-salt CHS in 2.0 ml 0.01M Tris-HCl, 0.1M KCl buffer.

(2) EPC-MLVs were prepared as described in Section 6.2.1. using 51.8 mg EPC in 2.0 ml 0.01M Tris-HCl, 0.1M KCl buffer.

(3) Multilamellar vesicles with a lipid bilayer composed of EPC and egg phosphatidic acid (EPA) were prepared using the method described in Section 6.2.1. for EPC-MLV preparation using 41.1 mg EPC and 9.79 mg EPA in 2.0 ml 0.01M Tris-HCl, 0.1M KCl buffer. The resulting MLVs (EPC:EPA-MLVs) comprised EPC:EPA in a 8:2 molar ratio respectively.

After vortical mixing, each suspension of MLVs (i.e., the CHS-MLVs, the EPC-MLVs and the EPC:EPA-MLVs) was allowed to stand at room temperature for two hours in the preparatory buffer. A 20 μl aliquot of each liposome preparation was then added to 1.0 ml of a series of 0.01M Tris-HCl buffers with KCl contrations ranging from 0.055M to 0.5M. After equilibration for one-half hour, light scattering was determined by measuring absorbance of the samples at a wavelength of 550 nm.

Figure 4:
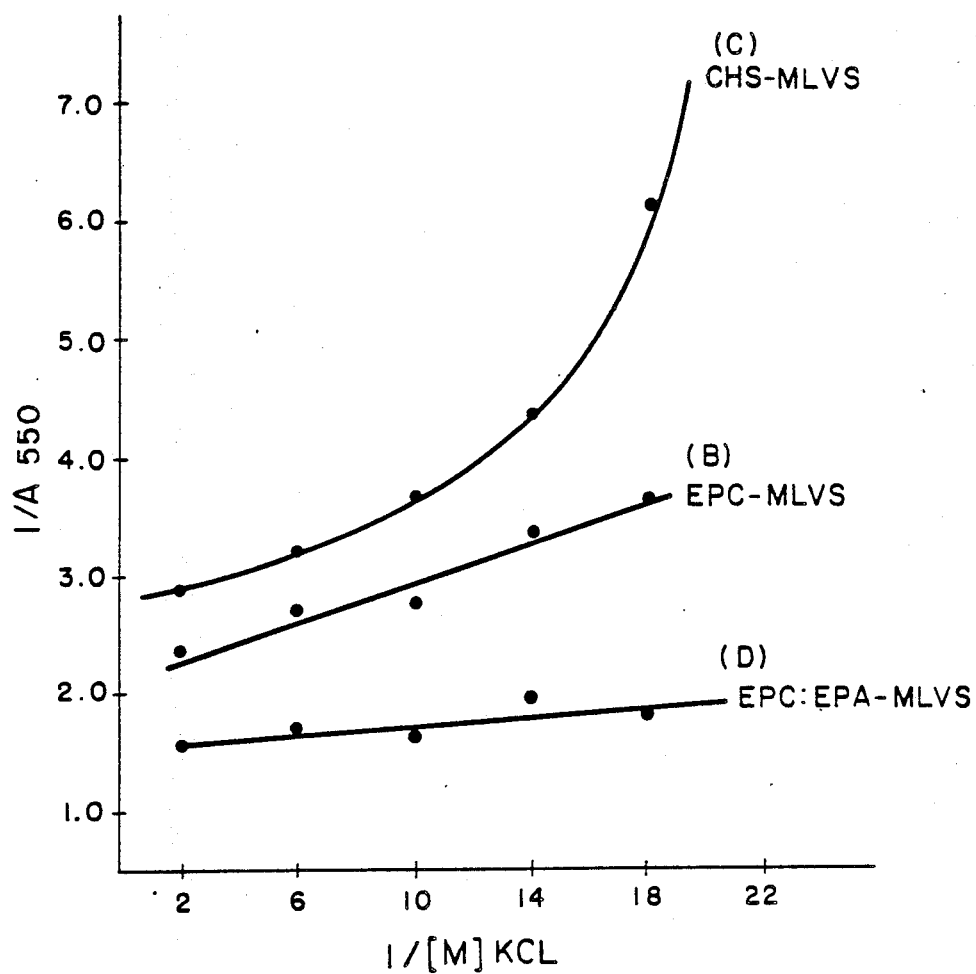
FIG. 4 graphically demonstrates the swelling profiles of cholesterol hemisuccinate liposomes and egg phosphatidylcholine liposomes in aqueous buffers of various tonicity.

Results are graphically illustrated in FIG. 4 in which absorbance is plotted against the inverse of the KCl concentrations of the media to which the vesicles are exposed. Increased absorbance indicates swelling of lipid vesicles. Curves B and D demonstrate that, as expected the phospholipid MLVs (i.e., EPC-MLVs, and EPC:EPA-MLVs) behaved as ideal osmometers. Curve C, however, indicates that although the CHS-MLVs behave as closed vesicular structures, they exhibit non-ideal behavior in hypo- and hypertonic media. This behavior, indicated in FIG. 4, is quite different than that observed in the cholesterol liposomes of Brockerhoff and Ramsammy (1982, Biochim. Biophys. Acta. 691: 227-232).

7. Example: Cholesterol Hemisuccinate Liposomes Entrapping Sparingly Soluble Compounds The entrapment in CHS-liposomes of compounds that are sparingly soluble in water is demonstrated for bovine growth hormone, insulin and tylosin.

7.1. Bovine Growth Hormone Entrapped in Cholesterol Hemisuccinate-SUVs

Bovine growth hormone (BGH), a simple protein composed of a single chain of approximately 191 amino acids, is partially water soluble. The normal solubility is 1 to 1.5 mg/ml at pH 8.0. BGH precipitates in organic solvents such as choloroform.

CHS-MLVs were prepared as described in Section 6.2 using 25 mg tris-salt CHS in 1.0 ml 0.01M Tris-HCl (pH 7.4), 0.14M NaCl buffer. The CHS-MLV preparation was sonicated to clarify to form sonicated CHS-SUVs and then either 5, 10, 15, 25, 30 or 166 mg BGH (Eli Lilly & Co., Indianapolis, Ind.) was added to separate aliquots of the sonicated CHS-SUV suspension. The suspensions were extensively mixed vortically, resulting in partitioning of the protein into the CHS-SUV bilayers. The sonicated CHS-SUV suspensions were visually observed for the presence of precipitate at 1, 2, and 21 days. No precipitate was observed, indicating that the bovine growth hormone remained entrapped in the CHS liposomes at all concentrations tested for 21 days at room temperature.

7.2. Insulin Entrapped in Cholesterol Hemisuccinate-SUVs

Zinc-insulin, a polypeptide hormone, although readily soluble in dilute acid or alkali, is practically insoluble in aqueous phases from pH 4.5 to 7.0. In fact the tendency of insulin solutions to form macroaggregates is an obstacle in the development of long-term insulin delivery systems.

CHS-MLVs were prepared as described in Section 6.2 using 25 mg tris-salt CHS in 1.0 ml 0.01M Tris-HCl (pH 7.4), 0.14M NaCl buffer. The CHS-MLV preparation was sonicated to clarify to form sonicated CHS-SUVs and up to 47 mg zinc-insulin powder (Boving Pancreatic Insulin, Sigma Chemical Co., St. Louis, Mo.) was added to the CHS-SUV suspension. The suspension was extensively mixed vortically, resulting in partitioning of the insulin into the CHS-SUV bilayers. The sonicated CHS-SUVs were visually observed for the presence of precipitate at 1, 2, and 21 days. No precipitate was observed indicating that insulin at a concentration of 5 mg/ml remains entrapped for at least 21 days at room temperature. Insulin entrapment occurs more rapidly at 37° C.

7.3. Tylosin Entrapped in Cholesterol Hemisuccinate-SUVs

Tylosin is an antibiotic that is soluble in water at 25° C. at 5 mg/ml, and is also soluble in lower alcohols, esters and ketones, chlorinated hydrocarbons, benzene, and ether.

Small unilamellar vesicles were prepared as follows: 100 mg tylosin-base (Eli Lilly & Co., Indianapolis, Ind.) and 200 mg tris-salt CHS were mixed vortically in 4 ml phosphate buffered saline (pH 7.4). The resulting milky suspension of CHS-MLVs was sonicated with a probe tip sonicator for 15 minutes. (As a precautionary measure, an ice bath was placed around the test tube to keep the temperature of the mixture down.) The mixture was then placed into a bath sonicator for 1 hour and 45 minutes.

After the 2 hour sonication period, the CHS-SUV entrapped tylosin was separated from the suspension by centrifugation of the suspension at $10,000 \times g$ for 10 minutes, forming a small pellet and an opalescent supernatant. The sonicated CHS-SUVs in the supernatant were visually compared to a suspension of 100 mg tylosin base (Eli Lilly & Co., Indianapolis, Ind.) added to the same volume of water. A precipitate formed in the suspension of tylosin base, however no precipitate formed in the CHS-SUV tylosin preparation. Thus the tylosin appeared to remain entrapped for at least 48 hours.

8. Example: The Use of Cholesterol Hemisuccinate Liposomes to Entrap Lipid Soluble Compounds The entrapment of lipid soluble bioactive agents is demonstrated for indomethacin and diazepam.

8.1. Indomethacin Entrapped in Cholesterol Hemisuccinate-MLVs

Indomethacin, a prostaglandin inhibitor, is practically insoluble in water. The free acid of indomethacin is soluble in ethanol, ether, acetone, and castor oil.

CHS-MLVs incorporating varying amounts of indomethacin as bioactive agent were prepared as follows: in a round-bottom flask, 25 mg tris-salt CHS, 1-5 mg indomethacin, and 10 $\mu$l $^{14}$C-indomethacin (22.0 mCi/mmol, New England Nuclear, Boston, Mass.) were combined. Sufficient methanol to dissolve all components was added. The mixture was then rotoevaporated to form a thin film on the vessel, and vacuum desiccated overnight to insure removal of all the methanol. Then CHS-MLVs were formed by adding 1.0 ml 0.01M Tris-HCl (pH 7.3), 0.14M NaCl buffer to each flask. The suspensions were mixed vortically with glass beads, and allowed to stand undisturbed for 2 hours.

After 2 hours, the relative amount of indomethacin entrapped in the CHS-MLVs was determined as follows: 9.0 ml 0.01M Tris-HCl (pH 7.3), 0.14M NaCl buffer was added to each sample and the mixture was centrifuged for 10-20 minutes at $10,000 \times g$. The resulting pellet was washed three times in 10 ml 0.01M Tris-HCl (pH 7.3), 0.14M NaCl buffer, and was suspended in a final volume of 1.0 ml 0.01M Tris-HCl (pH 7.3), 0.14M NaCl buffer. A "standard" was prepared in the same manner as the samples except that only radiolabeled indomethacin was added to the initial mixture (i.e., the 1 to 5 mg indomethacin was omitted from the CHS-MLV standard preparation). The radioactivity contained in filtered 20 $\mu$l aliquots from each sample were counted in 10 ml scintillation fluid. Comparison of the "standard" with the samples containing various concentrations of indomethacin permitted determination of the percentage of indomethacin entrapped. Results are presented in Table III.

TABLE III

ENTRAPMENT OF INDOMETHACIN IN CHS-MLVs

| Concentration Indomethacin (mg/ml) | % $^{14}$C-Indomethacin Entrapped in CHS-MLVs |
|---|---|
| 1 | 78 |
| 2 | 70 |
| 3 | 37 |
| 4 | 28 |
| 5 | 34 |

Results indicate that up to 78% of the indomethacin can be entrapped in CHS-MLVs.

8.1.2. Ultrastructure of Cholesterol Hemisuccinate Vesicles Containing Indomethacin In order to determine whether the entrapped indomethacin altered the membrane vesicles, the CHS-MLVs prepared in the presence of indomethacin (see Section 8.1.1.) were processed as previously described for freeze-etch electron microscopy. In freeze-etch electron microscopy, under low magnification, the "empty" CHS-MLVs wer indistinguishable from those that have indomethacin included. That is, there was no obvious feature that one can discern to be unique to one or the other. At high magnification, however, the "bilayer" of the CHS-MLVs containing indomethacin is distinctive. Because indomethacin is a water-insoluble drug and is soluble in ethanol, ether, acetone, and other non-polar solvents, it can be expected that the indomethacin, in the presence of lipids, would be arranged such that it was sequestered from the water. Examination of the bilayers seen by electron microscopy indicated that the thickness of the bilayers varies in the cross fracture. This suggested that the indomethacin was indeed distributed in the lipid portion of the bilayers, such that it appeared to give an added thickness and a very non-uniform configuration; that is, the thickness varied as one bilayer was traced along a fracture line. This effect is presumably special for those drugs whose solubilities are such that they sequester in the lipid portion of the bilayers.

8.2. Diazepam Entrapped in Cholesterol Hemisuccinate-SUVs

Diazepam, a sedative or tranquilizer (i.e., Valium) is soluble in chloroform, dimethylformamide, benzene, acetone and alcohol; it is only slightly soluble in water.

CHS-SUVs incorporating diazepam were prepared as follows: 2, 3, 4, or 5 mg diazepam was added to a test tube containing 5 μl $^3$H-diazepam (76.7 Ci/mmol, New England Nuclear, Boston, Mass.). Sufficient methanol was added to each tube to dissolve the drug (maximum 2 ml methanol). The mixture was then rotoevaporated to a thin film, and desiccated overnight under vacuum to insure removal of all the methanol. The dried film was resuspended in 1 ml of a suspension of sonicated CHS-SUVs (prepared as described below using 50, 100, or 200 mg/ml CHS), mixed vortically using glass beads and filtered using 0.22 μm Millipore filters (Millipore Corp., New York, N.Y.).

The CHS-SUVs were prepared according to the following protocol: 50, 100, or 200 mg tris-salt CHS was vortically mixed with 1.0 ml 0.01M Tris-HCl (pH 7.3), 0.14M NaCl buffer. Using a probe sonicator, the mixture was sonicated to an optical density of about 0.40 measured at a wavelength of 550 nm (i.e, a "clear" solution), and then centrifuged at 1,000×g to remove any titanium that might have come off the tip of the sonicator probe. The suspension of CHS-SUVs was then decanted from the tube.

The relative amount of diazepam that could be entrapped by the sonicated CHS-SUVs was determined by comparison of the samples with a "standard" preparation. The "standard" preparation was prepared in the same manner as the samples except that only radiolabeled diazepam was added (i.e, the 2 to 5 mg diazepam was omitted from the CHS-SUV standard preparation. In either case, the radioactivity contained in 10 μl aliquots of the filtered suspensions were counted in 10 ml scintillation fluid. Results are presented in Table IV.

TABLE IV

ENTRAPMENT OF DIAZEPAM IN SONICATED CHS-VESICLES

| Concentration Diazepam (mg/ml) | % $^3$H-Diazepam Entrapped Concentration CHS (mg/ml) | | |
|---|---|---|---|
| | 50 | 100 | 200 |
| 2 | 86 | 100 | 100 |
| 3 | 79 | 95 | 89 |
| 4 | 58 | 100 | 100 |
| 5 | 53 | 100 | 100 |

Results indicate that both 100 and 200 mg/ml CHS entrap 100% of the highest concentration of diazepam used (5 mg/ml). Since both 100 and 200 mg/ml CHS sufficiently entrap the diazepam, the 100 mg/ml represents a more ideal concentration of CHS for entrapment of diazepam.

9. Example: The Use of Cholesterol Hemisuccinate Liposomes to Determine Aminoglycoside Concentration in Serum It was observed that a relatively low concentration of CHS-vesicles (less than 1 μg/ml CHS) strongly agglutinated red blood cells (RBC) from a suspension in phosphate buffered saline (PBS). Since CHS-vesicles are precipitated by $Ca^{++}$ and other cations such as aminoglycoside antibiotics, the CHS-vesicles can be used to determine the concentration of aminoglycoside antibiotics in sera by:

(a) determining the dilution of serum containing antibiotic at which a fixed amount of CHS-vesicles are precipitated; and (b) Determining by hemagglutination-titration the concentration of the remaining free vesicles which are not precipitated after addition to the antibiotic-containing serum.

In both situations, the exact amount of antibiotic could be established using a comparison with a standard curve derived from known concentrations of antibiotic. The basic experiments are described below:

Accordingly, 24 μl of gentamycin sulfate in PBS (1 mg/ml) was serially diluted in serum (i.e., 25 μl aliquots of serum). Then a 24 μl aliquot of CHS-unilamellar vesicles prepared by sonicating tris-salt CHS at a concentration of 25 mg/ml in 0.01M Tris-HCl (pH 7.3), 0.14M NaCl buffer at pH 7.4, was added to each sample.

After about 10 minutes at room temperature, the turbidity of each mixture was recorded. Only mixtures containing 50 μg or more gentamycin showed a visible precipitation indicating that the CHS vesicles interacted with the gentamycin.

Next, the precipitated material was pelleted and the supernatant was used to determine the concentration of the CHS-SUVs by hemagglutination of chicken red blood cells. The hemagglutination assay was done in 96 U-shaped microwell plates by serially diluting the vesicle suspensions to 50 μl PBS and then adding in each well 40 μl of 0.5% RBC in PBS. After 60 minutes at 4° C., hemagglutination was observed with an inverted mirror. The control (RBC in the absence of CHS vesicles) showed no hemagglutination. All samples containing CHS strongly hemagglutinated the RBC with the exception of those which, in the previous experiment, were turbid. This result indicated that CHS vesicles interacted with gentamycin such that relatively fewer vesicles were available for hemagglutination in comparison with the control suspension containing only CHS.

10. Example: In Vivo Administration of Cholesterol Hemisuccinate Liposomes

The following subsections describe methods and compositions for the in vivo administration of bioactive agents using the cholesterol hemisuccinate liposomes of the present invention. The clinical effectiveness of the entrapped bioactive agent is determined, and drug distribution within selected organs is traced where appropriate.

10.1. Treatment of Joint Arthritis Using Indomethacin Entrapped in Cholesterol Hemisuccinate-MLVs Male white New Zealand rabbits (2 to 2.5 kg) were immunized intradermally, twice at two-week intervals, with 1 ml of 20 mg/ml bovine serum albumin (BSA) (Miles Laboratories, Elkhart, Ind.) emulsified in complete Freunds adjuvant. On the third week, the rabbits received a single intra-articular injection of 10 mg BSA in 1.0 ml of saline into the right knee joint to initiate joint arthritis. Left knee joints served as controls. The diameter of the joints was measured using a Fowler dial caliper, sensitive to 0.01 mm. The BSA-injected joints swell and typically measure 3 to 4 mm larger than control joints. On the fourth week, the rabbits received another intra-articular injection of BSA in saline to initiate joint inflammation.

CHS-MLVs were prepared as described in Section 8.1. using 270.0 mg CHS and 10 mg indomethacin, resulting in final concentration of 1.0 mg/ml indomethacin. Three days following induction of the inflammation, BSA-injected animals received a single intramuscular injection of the 1 mg/ml indomethacin entrapped in CHS-vesicles (total dose 1 mg/animal). Joint swelling was measured for another ten days.

Figure 5:
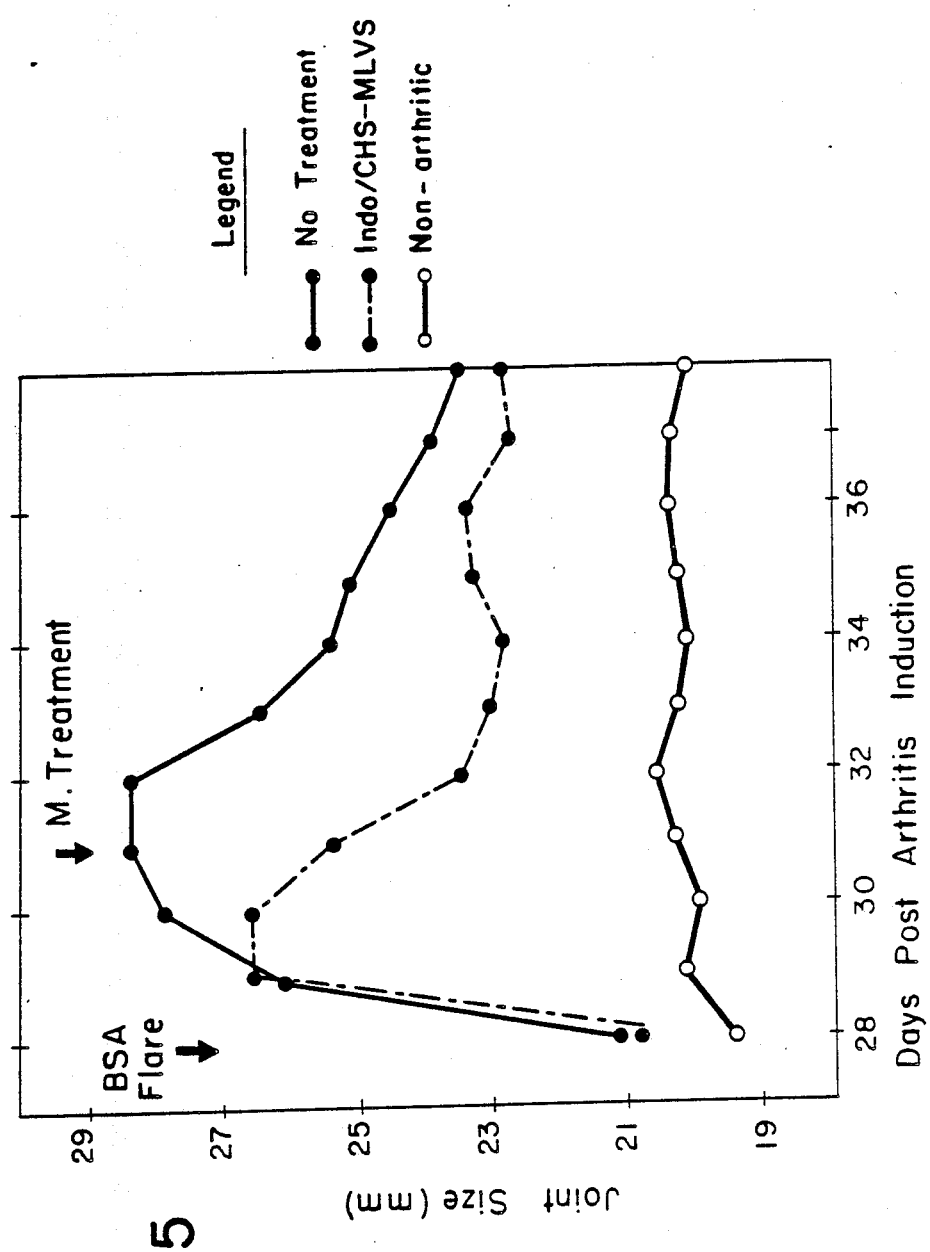
FIG. 5 graphically illustrates the effectiveness of indomethacin entrapped in cholesterol hemisuccinate liposomes in reducing joint swelling when administered intramuscularly.

Results illustrated graphically in FIG. 5, indicate that the indomethacin entrapped in CHS-MLVs was effective in reducing joint swelling when administered intramuscularly.

10.2. In Vivo Administration of Diazepam Entrapped in Cholesterol Hemisuccinate SUVs Mice were inoculated intravenously or intramuscularly with 500 μg/kg body weight of diazepam entrapped in CHS-SUVs prepared as described in Section 8.2. The diazepam had a sedative effect on the mice (the mice fell asleep after inoculation) indicating the retention of activity of the entrapped drug.

10.2.1. Organ Distribution After Intravenous Inoculation

CHS-SUVs containing entrapped diazepam were prepared as described in Section 8.2. After sonication in a bath sonicator, the absorbance of the suspension measured at a wavelength of 550 nm was 0.370. Then a 44.2 μl aliquot of the CHS-SUV suspension was added into a glass test tube, onto which 40 μCi of $^{14}$C-diazepam (specific activity is equal to 181 μCi/mg supplied as 100 μCi/ml in ethanol) had been dried down under nitrogen. After mixing vortically for five minutes, 1.282 ml of 0.01M Tris-HCl (pH 7.3), 0.14M NaCl buffer was added to the solution; resulting in a thirty-fold dilution of the suspension, yielding a therapeutic dose for the mice of 0.167 mg/μl diazepam.

A 0.1 ml aliquot of the CHS-SUV-$^{14}$C-diazepam suspension was injected into the tail vein of conscious, restrained 35 g Swiss-Webster mice. Control mice were similarly inoculated with an equivalent does of unentrapped $^{14}$C-diazepam. At 1, 2, or 5 hours post-injection, the mice were sacrificed by cervical dislocation and the internal organs (kidney, lung, spleen, liver, gut, brain, heart, pancreas, and fat) and a blood sample were removed. The organs were weighed and a small sample (20-40 μg) of each was digested and decolorized according to the method of Mahim and Kohberg (1966, Analytical Biochem. 16:500). The samples were then dark-adapted for five days to allow chemiluminescence to subside before the radioactivity was measured.

Figure 6:
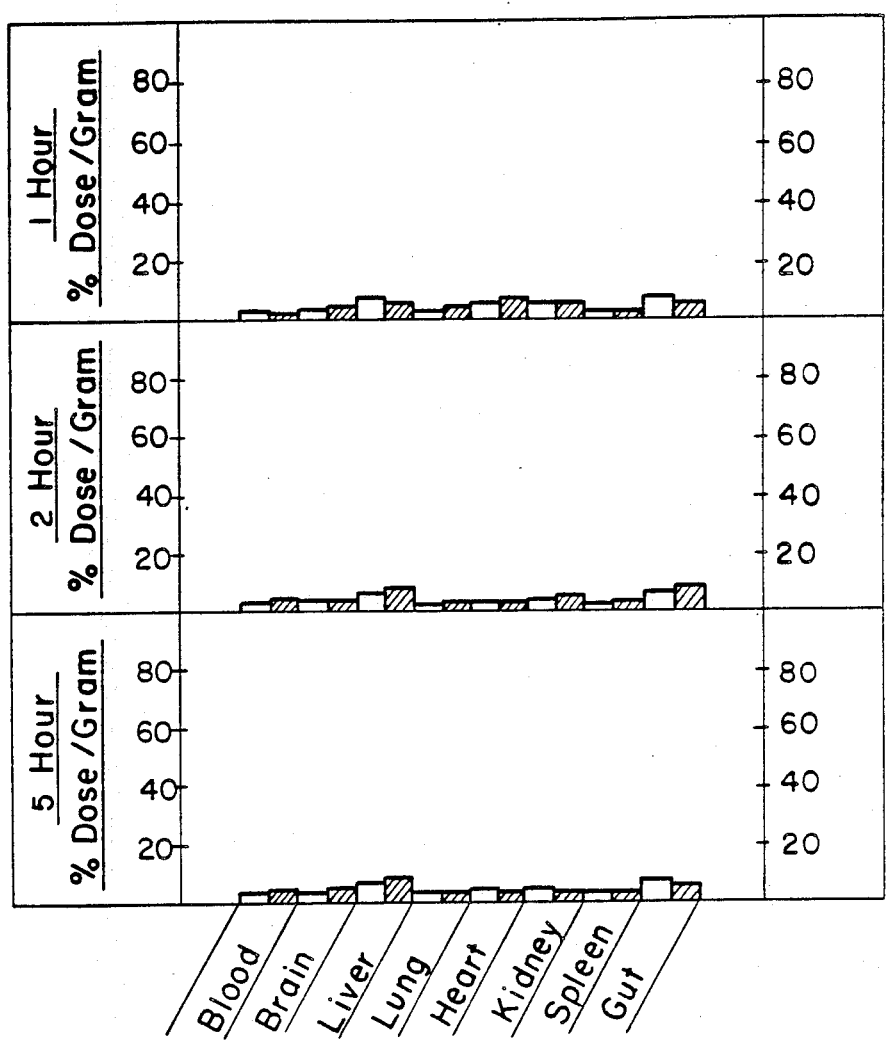
FIG. 6 represents the organ distribution of $^{14}C$-diazepam administered intravenously in mice either unencapsulated (free) or encapsulated in CHS-SUVs.

The results of this experiment are shown in FIG. 6. In the mice inoculated with the CHS-SUV entrapped diazepam, the drug does not accumulate in the spleen, indicating that the diazepam entrapped in CHS-SUVs does not behave like phospholipid liposome-entrapped drug when administered intravenously in vivo.

10.3. In Vivo Administration of Chromium Entrapped in Cholesterol Hemisuccinate-MLVs In order to determine whether CHS vesicles remain intact when administered in vivo, the organ distribution of a free aqueous marker as compared to that of the aqueous marker entrapped in CHS vesicles was determined after intravenous injection in mice. To this end, the organ distribution of unentrapped $^{51}$Chromium ($^{51}$Cr), $^{51}$Chromium entrapped in CHS-MLVs and $^{51}$Chromium entrapped in phospholipid vesicles were compared. The following protocols were followed:

(a) Unencapsulated $^{51}$Cr. $^{51}$Cr is supplied as $^{51}$CrO$_2$= in sterile 0.9% saline (New England Nuclear, Newton, Mass.). The free $^{51}$Cr injectate was made by diluting 100 μl $^{51}$Cr in 0.9% saline to 1.5 ml total volume with 0.01M Tris-HCl, pH 7.3, 0.14M NaCl, 5% dextrose. Sixteen 40 g male Swiss Webster mice each received a 0.1 ml (about 700,000 cpm) intravenous injection via the tail vein.

(b) $^{51}$Cr in CHS-MLVs were prepared by dissolving dry tris-salt CHS powder in 0.01M Tris-HCl, pH 7.3, 0.14M NaCl, 5% dextrose containing a trace amount of $^{51}$Cr ($^{51}$CrO$_2$= in sterile 0.9% saline). The mixture was vortically mixed and briefly then sonicated for 30 minutes. After pelleting by centrifugation and washing three times as previously described, the final pellet was resuspended to a final concentration of 10 mg/ml CHS, and sized at a 1 micron diameter by Nicomp quasielastic light scattering analysis. Twelve 40 g male Swiss Webster mice each received a 0.1 ml (about 120,000 cpm) intravenous injection via the tail vein.

(c) $^{51}$Cr in EPC-SPLVs were prepared by the general procedure described in detail in copending application Ser. No. 476,496, filed Mar. 24, 1983 and now U.S. Pat. No. 4,522,803 by Lenk et al. entitled "Stable Plurilamellar Vesicles, Their Preparation and Use", which is incorporated by reference herein. To this end, 5 ml batches were prepared by dissolving 65 mg egg phosphatidylcholine (EPC) in chloroform and drying down the EPC to form a film. The film was resuspended in 10 ml ether and 0.3 ml $^{51}$CrO$_2$= in 0.9% saline (pH 8) was added. The mixture was then emulsified by sonication while concurrently evaporating the ether under N$_2$ gas. The resulting stable plurilamellar vesicles (SPLVs) were resuspended in 5 ml 0.01M Tris-HCl, pH 7.3, 0.14M NaCl, 5% dextrose and pelleted by centrifugation. The pellet was washed three times to remove unentrapped $^{51}$Chromium and the final pellet was resuspended in 5 ml 0.01M Tris-HCl, pH 7.3, 0.14M NaCl, 5% dextrose. The final concentration of EPC was 13 mg/ml. Twelve 40 g male Swiss Webster mice each received a 0.1 ml (about 100,000 cpm) intravenous injection via the tail vein.

At the end of 1, 2, 5, and 24 hours 3 mice from each group treated with a liposome preparation and 4 mice from the group treated with unencapsulated $^{51}$Chromium were sacrificed by cervical dislocation. The organs were removed, rinsed with 0.9% saline, weighed and counted as previously described to determine the % dose and % dose/ram remaining in each organ tested.

Figure 7A:
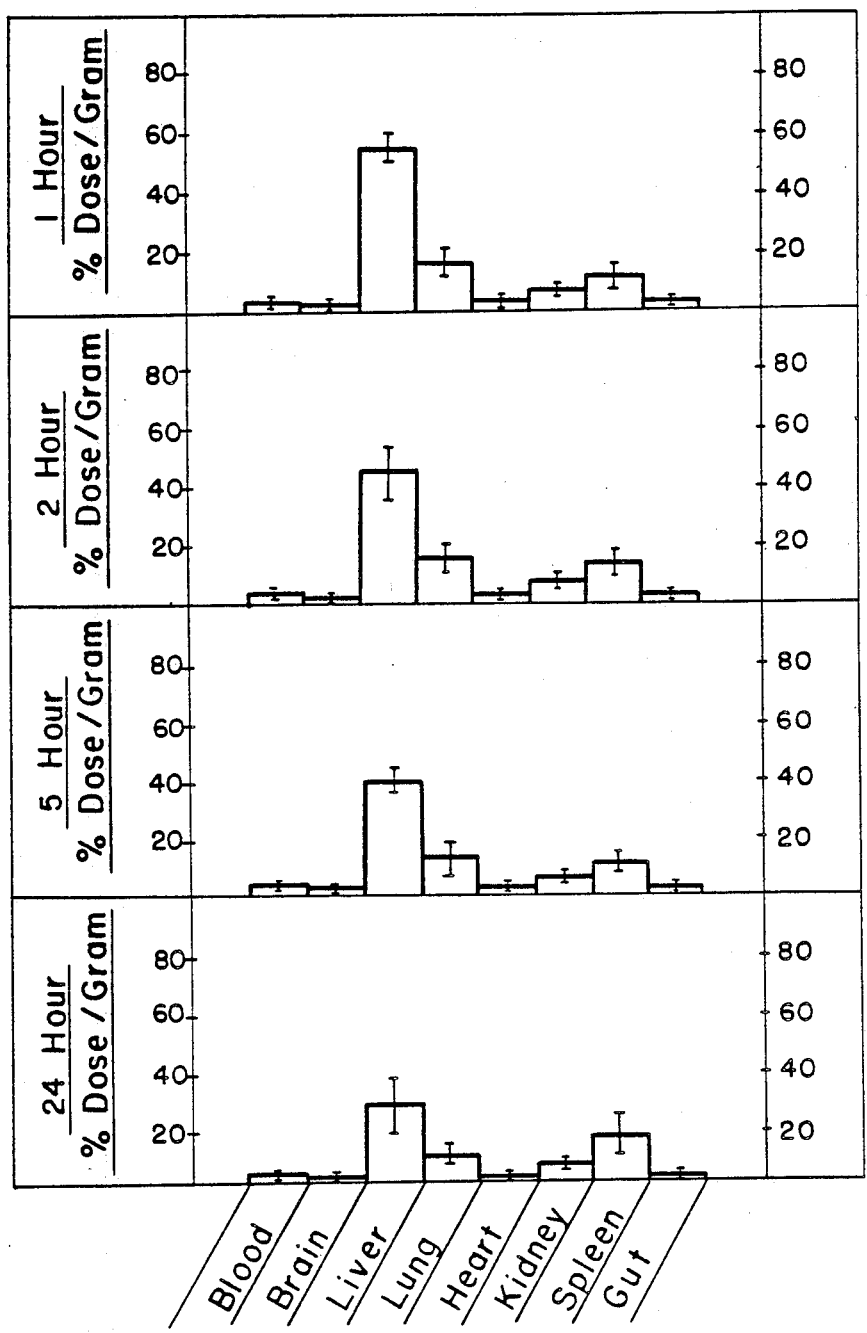
FIG. 7 A, B and C, represent the organ distribution of $^{51}Chromium$ administered intravenously in mice either, encapsulated in CHS-MLVs (FIG. 7A) or encapsulated in EPC-SPLVs (FIG. 7B) or unencapsulated (FIG. 7C).
Figure 7B:
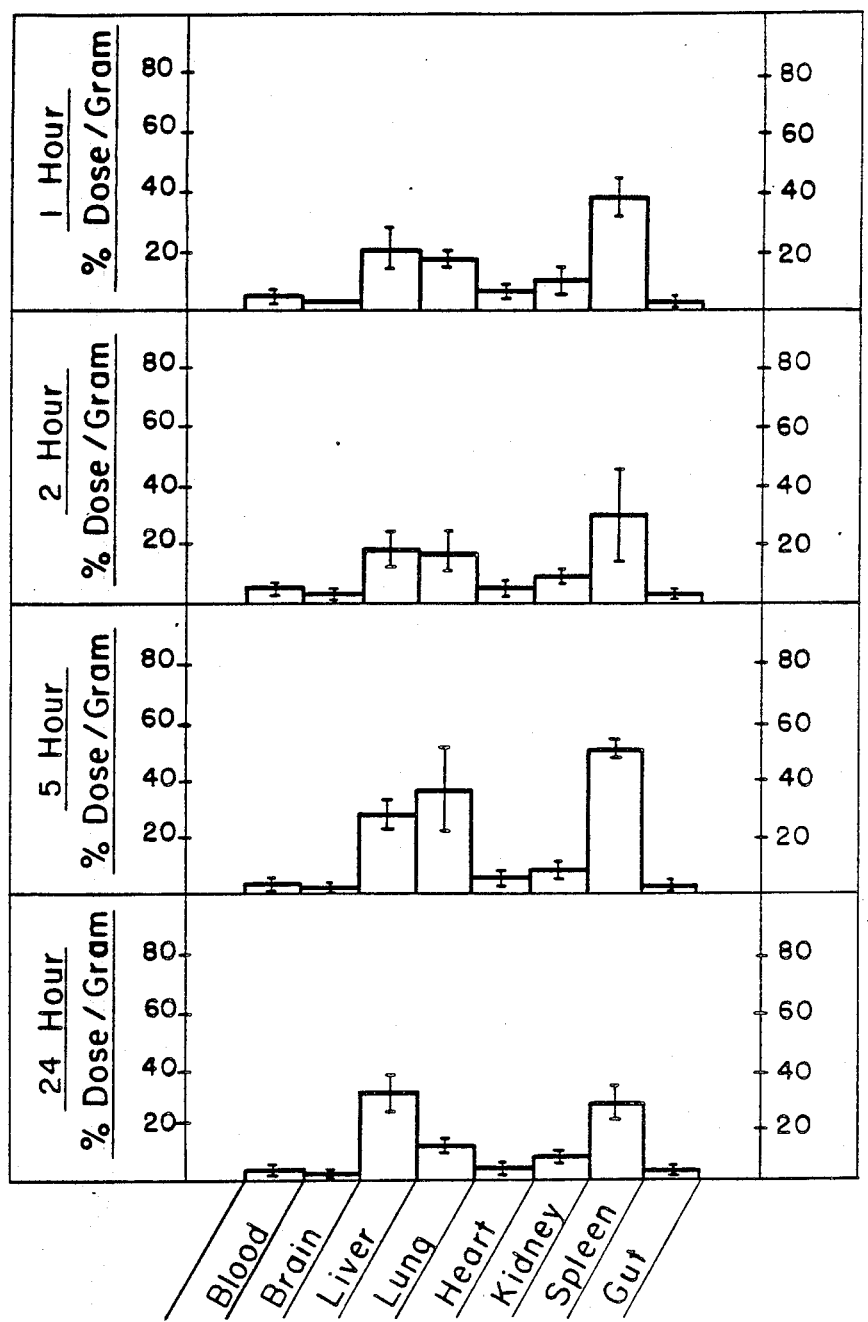
Figure 7C:
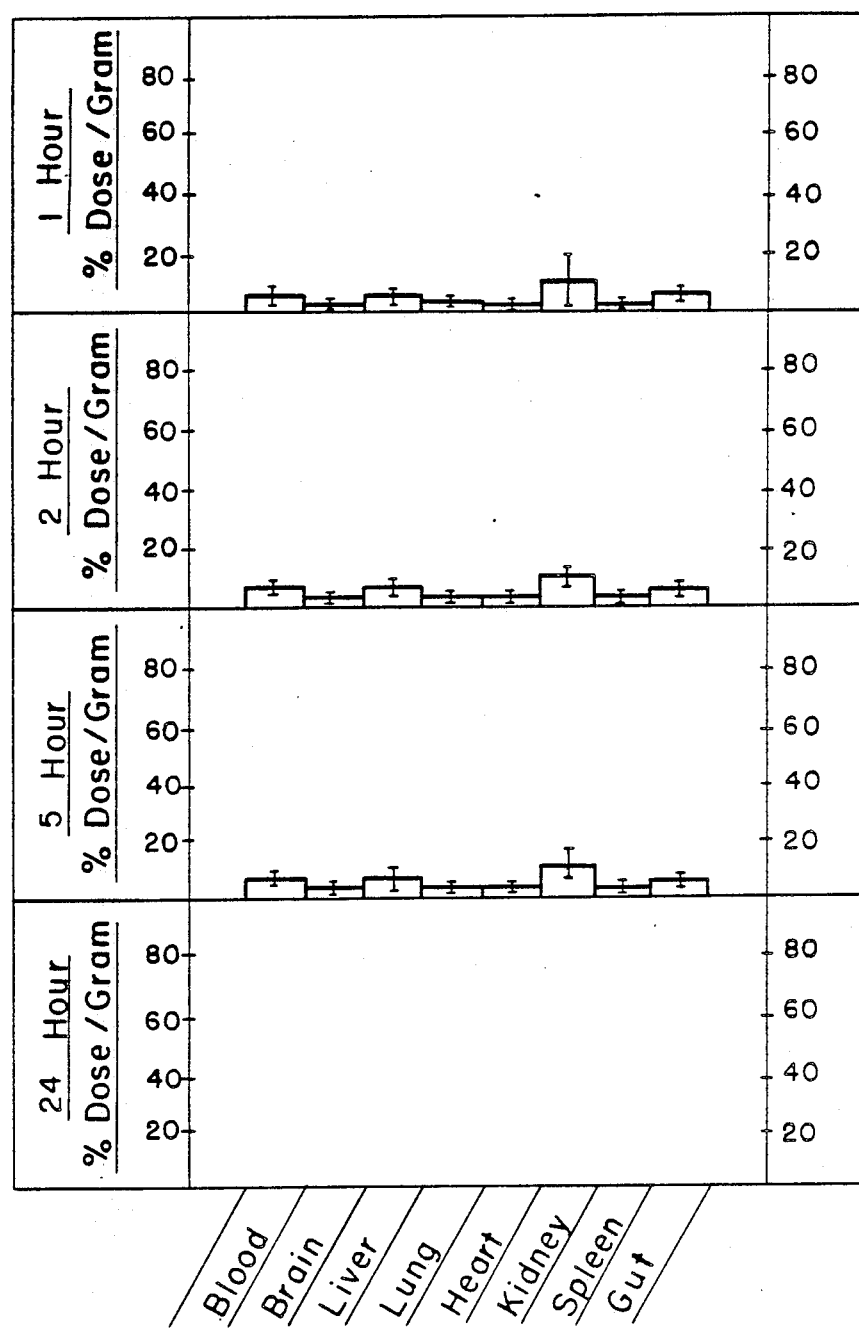

The results, shown in FIG. 7 demonstrate that unencapsulated chromium (see FIG. 7C) is excreted rapidly, and does not concentrate in any of the organs tested. EPC and CHS encapsulated chromium remains at measurable levels 24 hours after injection, indicating that CHS vesicles, like EPC-SPLVs, remain intact in vivo. Moreover, EPC-SPLVs (13 mg/ml) which have a mean diameter between 0.5 and 1.0 microns, accumulate in the liver, lung, and spleen (see FIG. 7B); i.e., the typical pattern of liposome distribution. Equimolar CHS vesicles accumulate primarily in the liver, and to a much lesser extent, in the lung and spleen (see FIG. 7A). Indicating a difference in the distribution pattern of the two liposome preparatins in vivo.

10.4. In Vivo Administration of Human Growth Hormone Entrapped in Cholesterol Hemisuccinate MLVs CHS-multilamellar vesicles incorporating $^{125}$I-human growth hormone (HGH, New England Nuclear, Boston, Mass.) were prepared as follows: tris-salt CHS was added to 0.01M Tris-HCl, 0.14M NaCl buffer (pH 7.4) containing 1 μCi/ml $^{125}$I-HGH (New England Nuclear, Boston, Mass.) to yield a final concentration 25 mg/ml tris-salt CHS. The suspension was mixed vortically with glass beads. The resulting CHS-MLVs entrapped 10% of the $^{125}$I-HGH as determined by a comparison of the initial radioactive counts.

A group of 12 female Swiss-Webster mice were injected intramuscularly in the hind limb with 0.5 ml of the CHS-MLV entrapped $^{125}$I-HGH suspension. A control group of 12 mice were injected with 0.5 ml free $^{125}$I-HGH in 0.01M Tris-HCl, 0.14M NaCl buffer. Each animal in both groups received approximately 35,000 cpm/animal. At periodic intervals post-injection, the mice were sacrificed, the hind limb dissected, and percent total radioactivity remaining was determined. The data in Table V demonstrate substantial increase in retention of $^{125}$I-HGH when incorporated into CHS-MLVs. Thus, when injected intramuscularly, the CHS-liposome entrapped drug is released in a sustained fashion.

TABLE V

RETENTION OF ADMINISTERED MLV-ENTRAPPED $^{125}$I-HUMAN GROWTH HORMONE

| Inoculum | % Radioactivity Remaining in Limb Time (Hours) | | | |
|---|---|---|---|---|
| (N = 12 animals) | 3 | 24 | 72 | 168 |
| Control[a] $^{125}$I-HGH | 5 | 0.7 | 0.2 | 0.3 |
| $^{125}$-I-HGH in | 56 | 37 | 29 | 22 |

TABLE V-continued

RETENTION OF ADMINISTERED MLV-ENTRAPPED $^{125}$I-HUMAN GROWTH HORMONE

| Inoculum | % Radioactivity Remaining in Limb Time (Hours) | | | |
|---|---|---|---|---|
| (N = 12 animals) | 3 | 24 | 72 | 168 |
| CHS-vesicles[b] | | | | |

[a]Animals received 0.5 ml $^{125}$I-Human Growth Hormone in 0.01 M Tris-HCl, 0.14 M NaCl.
[b]Animals received 0.5 ml $^{125}$I-Human Growth Hormone in CHS-vesicles (25 mg/ml CHS) in 0.01 M Tris-HCl, 0.14 M NaCl.

What is claimed is:

1. Steroidal liposomes comprising completely closed bilayers comprising a salt form of an organic acid derivative of a sterol in which the salt is derived from an ionizable bioactive agent which is an antifungal compound.

2. Steroidal liposomes according to claim 1 in which the antifungal compound is terconazole.

3. Steroidal liposomes comprising a salt form of an organic acid derivative of a sterol wherein said salt has comprises a cation and an anion the cation of which is an aminoglycoside antibiotic.

4. Steroidal liposomes comprising completely closed bilayers comprising a salt form of an organic acid derivative of a sterol wherein the bilayers comprise a tris(hydroxymethyl)-aminoethane salt form of a hemisuccinate derivative of cholesterol and a bioactive agent which comprises an aminoglycoside antibiotic.

5. Steroidal liposomes comprising completely closed bilayers comprising a salt form of an organic acid derivative of a sterol wherein the bilayers comprise a triethanolamine.

6. A steroidal liposome comprising a bioactive agent, and wherein bilayers of the liposome comprise a salt form of a carboxylic acid derivative of a sterol, a salt form of a dicarboxylic acid derivative of a sterol, a salt form of a polycarboxylic acid derivative of a sterol, a salt form of an hydroxyl carboxylic acid derivative of a sterol, a salt form of an aminoacid derivative of a sterol, or a salt form of a poly(amino acid) derivative of a sterol; or a salt form of an organic acid derivative of cholesterol, a vitamin D, a phytosterol, or a steroidal hormone.

7. The steroidal liposome of claim 6 wherein the bilayers of the liposome comprise a salt form of a carboxylic acid derivative of a sterol, a salt form of a dicarboxylic acid derivative of a sterol, a salt form of a polycarboxylic acid derivative of a sterol, a salt form of an hydroxyl carboxylic acid derivative of a sterol, a salt form of an aminoacid derivative of a sterol, or a salt form of a poly(amino acid) derivative of a sterol.

8. The steroidal liposome of claim 7 wherein the dicarboxylic acid comprises an aliphatic dicarboxylic acid of up to seven carbon atoms.

9. The steroidal liposome of claim 8 wherein the aliphatic dicarboxylic acid is succinate.

10. The steroidal liposome of claim 8 wherein the bilayers of the liposome comprise a salt form of an organic acid derivative of cholesterol, a vitamin D, a phytosterol, or a steroidal hormone.

11. The steroidal liposome of claim 6 comprising a bioactive agent wherein the bilayers of the liposome comprise the tris(hydroxymethyl)aminomethane salt form of a hemisuccinate derivative of cholesterol and wherein the bioactive agent is a growth hormone, bovine growth hormone, human growth hormone, insulin, a dye, an anti-inflammatory compound, an anxiolytic agent or a vitamin.

12. The steroidal liposome of claim 11 wherein the bilayers of the liposome comprise the tris(hydroxymethyl)aminomethane salt form of a hemisuccinate derivative of cholesterol wherein the liposome comprises a multilamellar vesicle.

13. The steroidal liposome of claim 11 wherein the bilayers of the liposome comprise the tris(hydroxymethyl)aminomethane salt form of a hemisuccinate derivative of cholesterol wherein the liposome comprises a unilamellar vesicle.

14. The steroidal liposome of claim 11 wherein the bilayers of the liposome comprise the tris(hydroxymethyl)aminomethane salt form of a hemisuccinate derivative of cholesterol wherein the bioactive agent comprises an antibacterial compound.

15. The steroidal liposome of claim 14 wherein the bilayers of the liposome comprise the tris(hydroxymethyl)aminomethane salt form of a hemisuccinate derivative of cholesterol wherein the antibacterial agent comprises tylosin.

16. The steroidal liposome of claim 11 wherein the bioactive agent comprises a growth hormone.

17. The steroidal liposome of claim 16 wherein the hormone comprises bovine growth hormone.

18. The steroidal liposome of claim 16 wherein the hormone comprises human growth hormone.

19. The steroidal liposome of claim 11 wherein the bioactive agent comprises insulin.

20. The steroidal liposome of claim 11 wherein the bioactive agent comprises immunoglobulin.

21. The steroidal liposome of claim 11 wherein the bioactive agent comprises a dye.

22. The steroidal liposome of claim 11 wherein the bioactive agent comprises an anti-inflammatory compound.

23. The steroidal liposome of claim 22 wherein the antiinflammatory compound is indomethacin.

24. The steroidal liposome of claim 11 wherein the bioactive agent comprises a psychoactive or anxiolytic agent.

25. The steroidal liposome of claim 24 wherein the psychoactive or anxiolytic agent comprises diazepam.

26. The steroidal liposome of claim 11 wherein the bioactive agent comprises a vitamin.

27. The steroidal liposome of claim 26 wherein the vitamin comprises alpha-tocopherol.

28. Steroidal liposomes comprising completely closed bilayers comprising a salt form of an organic acid derivative of a sterol and a bioactive agent wherein the bioactive agent comprises growth hormone, insulin, immunoglobulin, dye, anti-inflammatory compounds, anxiolytic agent or a vitamin.

29. A steroidal liposome of claim 28 wherein the bioactive agent comprises an antifungal compound.

30. An intravaginal pharmaceutical preparation comprising the steroidal liposome of claim 29.

31. A topical or oral pharmaceutical preparation comprising the steroidal liposome of claim 29.

32. The steroidal liposome of claim 29 wherein the antifungal compound comprises miconazole, econazole, isoconazole, tioconazole, bifonazole, clotrimazole, butaconazole, itraconazole, oxiconazole, fenticonazole, nystatin, naftifine, amphotericin B, zinoconazole, terconazole or ciclopirox olamine.

33. The steroidal liposome of claim 32 wherein the bioactive agent comprises miconazole or terconazole.

34. The steroidal liposome of claim 33 wherein the liposome is in intravaginal dosage form.

35. Steroidal liposomes comprising completely closed bilayers comprising a salt form of an organic acid derivative of a sterol and a bioactive agent wherein the bioactive agent is an antifungal compound, antibacterial agent, antiviral agent agent or anti-parasitic agent.

36. Steroidal liposomes comprising completely closed bilayers comprising a salt form of an organic acid derivative of a sterol and a bioactive agent wherein the bioactive agent is a tumoricidal agent or anti-metabolite.

37. Steroidal liposomes comprising completely closed bilayers comprising a salt form of an organic acid derivative of a sterol and a bioactive agent wherein the bioactive agent is an immunomodulator, peptide, protein, or polypeptide.

38. Steroidal liposomes comprising completely closed bilayers comprising a salt form of an organic acid derivative of a sterol and a bioactive agent wherein the bioactive agent is an antiglaucomic agent, vasodilator, toxin or enzyme.

39. Steroidal liposomes comprising completely closed bilayers comprising a salt form of an organic acid derivative of a sterol and a bioactive agent wherein the bioactive agent is a neurotransmitter, glycoprotein, or lipoprotein.

40. Steroidal liposomes comprising completely closed bilayers comprising a salt form of an organic acid derivative of a sterol and a bioactive agent wherein the bioactive agent is a radiolabel, radio-opaque compound or fluorescent compound.

41. Steroidal liposomes comprising completely closed bilayers comprising a salt form of an organic acid derivative of a sterol and a bioactive agent wherein the bioactive agent is a mydriatic, receptor binding molecule, local anesthetic or narcotic.

42. Steroidal liposomes comprising completely closed bilayers comprising a salt form of an organic acid derivative of a sterol and a bioactive agent wherein the bioactive agent is a nucleic acid or polynucleotide.

43. Steroidal liposomes comprising completely closed bilayers comprising a salt form of an organic acid derivative of a sterol and a bioactive agent wherein the sterol is cholesterol and the organic acid derivative is hemisuccinate.

44. A method for administering an antifungal compound in vivo comprising, administering to a host the compound entrapped in a liposome, the bilayers of which comprise a salt form of an organic acid derivative of a sterol, wherein the compound is administered intravaginally, orally or topically.

45. The method according to claim 44 wherein the antifungal compound is miconazole or terconazole.

46. A method for administering an antifungal compound in vivo comprising, administering to a host the compound entrapped in a liposome, the bilayers of which comprise a salt form of an organic acid derivative of a sterol, wherein the antifungal compound is econazole, isoconazole, tioconazole, bifonazole, clotrimazole, butaconazole, itraconazole, oxiconazole, fenticonazole, nystatin, naftifine, amphotericin B, zinoconazole, terconazole or ciclopirox olamine.

* * * * *